(12) United States Patent
Ruiz

(10) Patent No.: US 6,302,877 B1
(45) Date of Patent: *Oct. 16, 2001

(54) APPARATUS AND METHOD FOR PERFORMING PRESBYOPIA CORRECTIVE SURGERY

(76) Inventor: Luis Antonio Ruiz, Centro Oftalmólogico Colombiano, Carrera 20 No. 85-11, Pisos 5o. -6o., Santafé de Bogotá, D.C. (CO)

( * ) Notice: Subject to any disclaimer, the term of this patent is extended or adjusted under 35 U.S.C. 154(b) by 0 days.

This patent is subject to a terminal disclaimer.

(21) Appl. No.: 09/186,884

(22) Filed: Nov. 6, 1998

Related U.S. Application Data

(63) Continuation-in-part of application No. 08/660,376, filed on Jun. 7, 1996, now Pat. No. 5,928,129, which is a continuation-in-part of application No. 08/268,182, filed on Jun. 29, 1994, now Pat. No. 5,533,997.

(51) Int. Cl.[7] ........................................ H61N 5/06
(52) U.S. Cl. ................................................. 606/5
(58) Field of Search ................... 606/3, 5, 7, 10

(56) References Cited

U.S. PATENT DOCUMENTS 4,173,980 11/1979 Curtain .

(List continued on next page.)

FOREIGN PATENT DOCUMENTS

A-346116 12/1989 (EP) .

(List continued on next page.)

OTHER PUBLICATIONS

*Lasers in Surgery and Medicine*, vol. 10, No. 5, Jan. 1, 1990, pp. 463–468, XP 000385912, Pallikaris: "Laser In–Situ Keratomileusis".

(List continued on next page.)

*Primary Examiner*—Robert L. Nasser, Jr.

(57) ABSTRACT

A system and process for correcting presbyopia with the system including a tissue removal system that preferably includes a laser system with means for forming a predetermined presbyopia correction contour corresponding to a predetermined ablation profile through controlled ablation of an exposed corneal stroma area of the eye such that a central zone of about 1–3 mm or, more preferably, 1.4 to 1.8 mm is left intact with a main, maximum presbyopia ablation zone bordering the untouched or hardly touched (e.g., a radiused transition edge) central zone. The annular maximum ablation zone in the stroma is defined by a smoothly curving, steep profile section which extends out from a central, non-ablation section of the profile. Further outward from the maximum ablation zone in the stroma is an annular treatment zone that is determined by a further section of the presbyopia correcting profile generally represented by a smoothing transition section that extends into another zone which is an unablated zone. The method and device for controlling the formation of the desired corneal stroma configuration preferably involves a presbyopic corrective module based on a predetermined profile determining equation that utilizes certain inputs which preferably include values determined by eye measurements and, preferably, also values pulled from a plurality of zone diameter ranges and a range for maximum depth. The manner in which this profile controlling information is implemented in the ablation or tissue removal process is preferably provided by modification of a present control system of one or more preexisting laser systems such as those used in hyperopia and myopia correction procedures. This modification can include, for example, an added software or hardware module, the formation of a mask with or without a mask movement assembly, or the formation of a suitable mold or shaping device for forming, for example, an erodible mask that can input the desired contour to the exposed corneal stroma. The system and apparatus of the present invention also preferably involve a microkeratome or the like for forming resections in the eye to expose the corneal stroma. A positioning marker, cleaning system and drying system are also preferably used in the present invention to facilitate, for example, corneal flap formation, laser positioning, flap repositioning on a clean surface following ablation and providing a dry corneal stroma surface to the ablating laser. With the system and method of the present invention there is provided a way to efficiently and safely correct problems associated with presbyopia while retaining good near and far vision capabilities and with reduced undesirable post-operative symptoms.

56 Claims, 7 Drawing Sheets

U.S. PATENT DOCUMENTS

| | | |
|---|---|---|
| 4,461,294 | 7/1984 | Baron . |
| 4,660,556 | 4/1987 | Swinger et al. . |
| 4,662,370 | 5/1987 | Hoffmann et al. . |
| 4,665,914 | 5/1987 | Tanne . |
| 4,674,503 | 6/1987 | Peyman et al. . |
| 4,688,570 | 8/1987 | Kramer et al. . |
| 4,705,035 | 11/1987 | Givens . |
| 4,718,418 | 1/1988 | L'Esperance, Jr. . |
| 4,729,372 | 3/1988 | L'Esperance, Jr. . |
| 4,770,172 | 9/1988 | L'Esperance, Jr. . |
| 4,773,414 | 9/1988 | L'Esperance, Jr. . |
| 4,798,204 | 1/1989 | L'Esperance, Jr. . |
| 4,840,175 | 6/1989 | Peyman . |
| 4,856,513 | 8/1989 | Muller . |
| 4,880,017 | 11/1989 | Soll . |
| 4,903,695 | 2/1990 | Warner et al. . |
| 4,907,586 | 3/1990 | Bille et al. . |
| 4,941,093 | 7/1990 | Marshall et al. . |
| 4,988,348 | 1/1991 | Bille . |
| 5,009,660 | 4/1991 | Clapham . |
| 5,019,074 | 5/1991 | Muller . |
| 5,133,726 | 7/1992 | Ruiz et al. . |
| 5,152,759 | 10/1992 | Parel et al. . |
| 5,163,934 | 11/1992 | Munnerlyn . |
| 5,207,668 | 5/1993 | L'Esperance, Jr. . |
| 5,246,435 | 9/1993 | Bille et al. . |
| 5,263,951 | 11/1993 | Spears et al. . |
| 5,314,422 | 5/1994 | Nizzola . |
| 5,324,281 | 6/1994 | Muller . |
| 5,395,356 | * 3/1995 | King et al. ................................ 606/5 |
| 5,437,658 | 8/1995 | Muller et al. . |
| 5,439,462 | 8/1995 | Bille et al. . |
| 5,529,076 | * 6/1996 | Schachar .................................. 606/5 |
| 5,533,997 | 7/1996 | Ruiz . |
| 5,647,865 | * 7/1997 | Swinger .................................... 606/5 |
| 5,651,784 | 7/1997 | Klopotek . |
| 5,803,923 | * 3/1995 | Singh-Derewa et al. ................. 606/5 |
| 5,806,530 | * 9/1998 | Herrick .................................... 606/5 |
| 5,865,830 | 2/1999 | Parel et al. . |

FOREIGN PATENT DOCUMENTS

| | | |
|---|---|---|
| A-402250 | 12/1990 | (EP) . |
| 0 417 952 | 3/1991 | (EP) . |
| 3-155491 | 7/1991 | (JP) . |
| 3-94750 | 4/1992 | (JP) . |
| 6-181944 | 7/1994 | (JP) . |
| WO 94/01067 | 1/1994 | (WO) . |

OTHER PUBLICATIONS

Steinway Instrument Co., The Steinway/Barraquer In–Situ Microkeratome Set, from the Steinway Instrument Co. of San Diego, California.

*Surgery For Hyperopia & Presbyopia*, by Neal A. Sher, M.D., F.A.C.S., Williams & Wilkins, 1997 (entire book submitted).

* cited by examiner

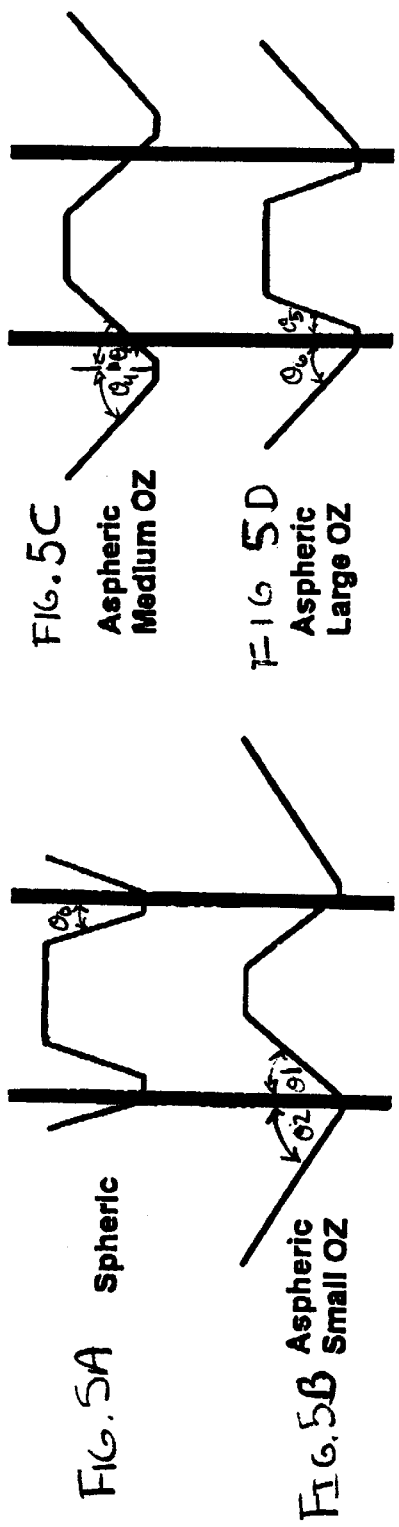
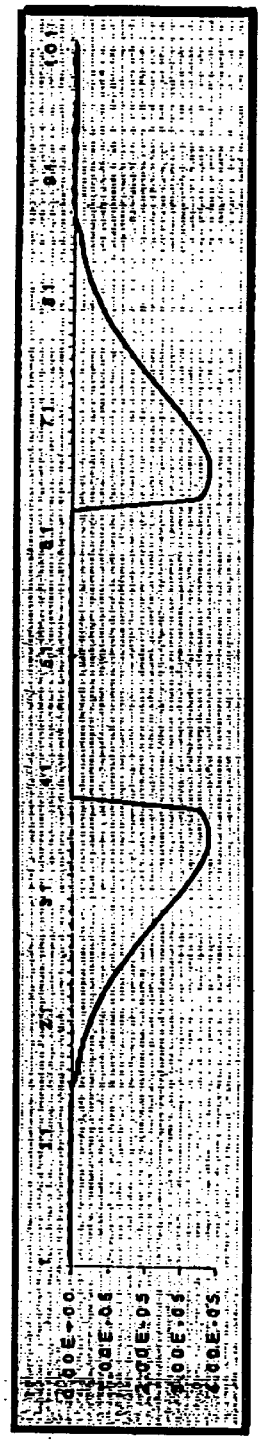

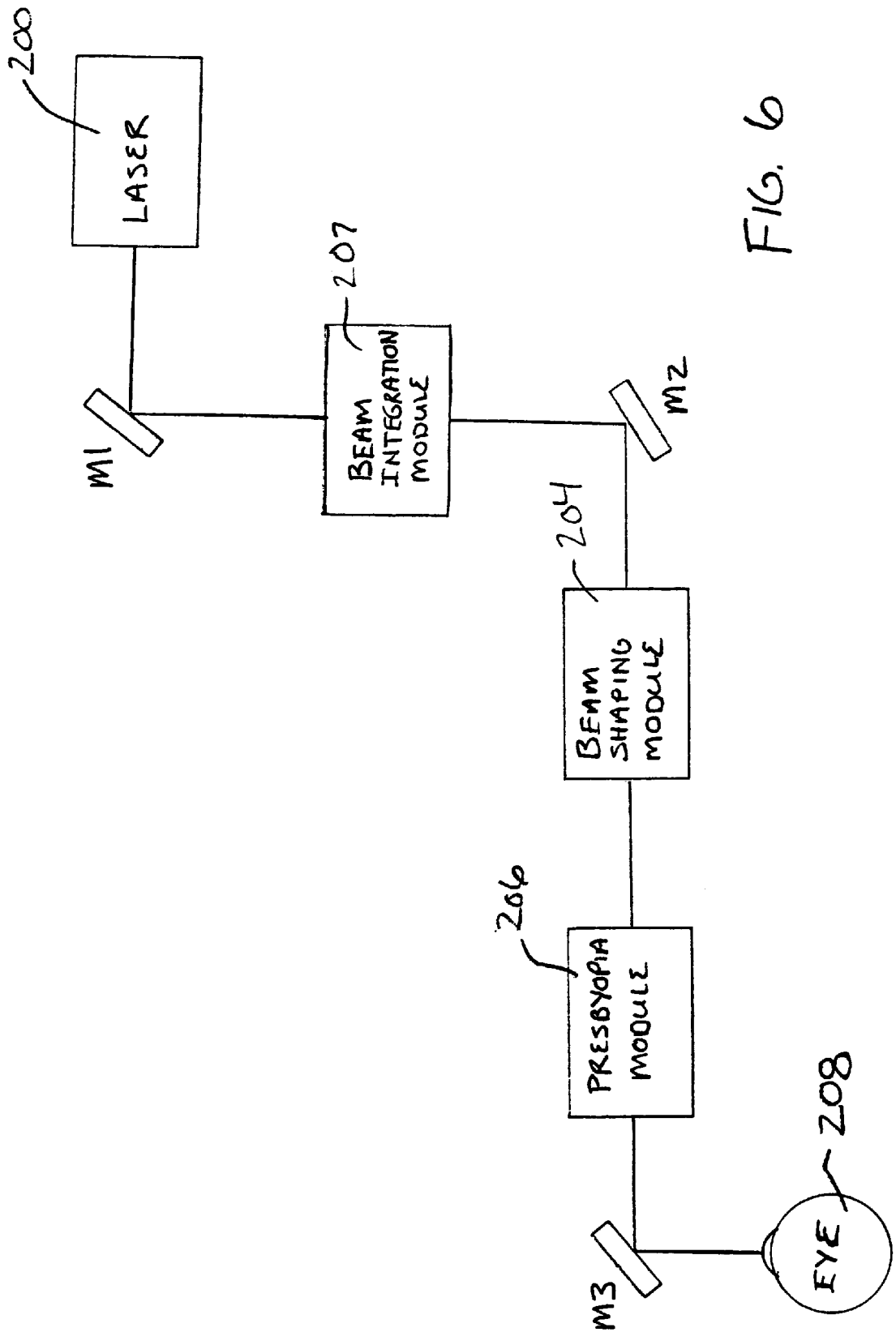

APPARATUS AND METHOD FOR PERFORMING PRESBYOPIA CORRECTIVE SURGERY

REFERENCE TO A RELATED APPLICATION

This application is a continuation-in-part of U.S. patent application Ser. No. 08/660,376 filed on Jun. 7, 1996 (now U.S. Pat. No. 5,928,129), which is a continuation-in-part of U.S. patent application Ser. No. 08/268,182 filed on Jun. 29, 1994 (now U.S. Pat. No. 5,533,997) and each of these applications are incorporated by reference.

FIELD OF THE INVENTION

The invention relates to a system and method for correcting presbyopia through a reshaping of the eye's corneal curvature, so as to have a desired corrective corneal curvature based upon a predetermined eye material removal profile. The removal of eye material is carried out in the corneal stroma preferably with a laser system with means for forming a sculptured corneal stroma having the predetermined profile in cross-section, which profile is based on a predetermined profile equation and the specific input of parameters including measurable eye parameters. The laser system includes control means which relies on corrective presbyopia directive means for ablative resculpturing of the corneal stroma, which directive means facilitates formation of the presbyopia correcting profile deemed best suited for the patient based on preestablished profile parameters.

BACKGROUND OF THE INVENTION

For many, many years, humans have sought ways to correct visual problems. The ancient Chinese slept with small bags of mercury on their eyes, flattening their corneas and improving their shortsightedness. Unfortunately, the effects only worked for a few minutes after waking. Spectacles are thought to have been first introduced by the Arabs in the 11th Century and were introduced into Europe about 200 years later. This century has seen the development of contact lenses, initially the hard variety and later soft and disposable soft lenses.

Although these optical aids allow patients to see well while wearing them, they do not offer a permanent cure for the visual disorder or problem. Also, in many situations, they are inappropriate, for example, when swimming or wearing contacts in the laboratory. Another problem is that in some instances dangerous situations can arise when they become dislodged. This can occur while they are being used by firefighters and police officers.

Roughly two decades ago, surgical techniques were introduced in an effort to permanently correct shortsightedness and astigmatism. The radial keratotomy procedure used a diamond blade to make incisions into the cornea, the front surface or "window of the eye". Although this technique worked well, there have been problems with long term stability of vision and weakening of the cornea as a result of the cuts often having to be made up to 95% of the corneal thickness.

More recently, these older techniques have been replaced with laser treatment techniques which have replaced the surgeon's blade with a computer controlled laser that gently re-sculptures the shape of the cornea without cutting or weakening the eye. These laser techniques are typically carried out with a photoablation process using an excimer laser.

Excimer lasers were chiefly developed for the manufacture of computer microchips, where they were used to etch the circuits. However, the laser's extreme accuracy resulted in it being well suited as an eye laser. That is, many eye lasers are extremely accurate and remove only 0.25 microns ($\frac{1}{4000}^{th}$ millimeter) of tissue per pulse. During the re-sculpturing, the excimer laser gently "evaporates" or vaporizes tissue; there is no burning or cutting involved. In most cases, the laser treatment takes only 20 to 45 seconds, depending on how severe the refractive error is.

In the normal eye, light rays entering the eye are accurately focused on the retina and a clear image is formed. Most of the bending or focusing of the light rays occurs at the cornea, with the natural lens inside the eye being responsible for fine adjustments. If light is not focused on the retina, then the eye is said to have a refractive error. Common refractive errors include: myopia or shortsightedness, hyperopia or farsightedness, and astigmatism. The excimer laser has been used to accurately re-sculpture the cornea in myopia, hyperopia and astigmatism corrections in an effort to make the curve of the cornea focus light rays normally on the retina.

Myopia, or shortsightedness, is a condition whereby light rays come to a focus in front of, rather than on, the retina at the back of the eye. This results in blurry vision, especially when looking at objects far away. Myopia results from the length of the eye being too long or the cornea being too steeply curved.

In hyperopia, or farsightedness, light rays are focused behind the retina. This results in blurry vision especially when looking at objects that are close. Hyperopia results from the length of the eye being too short or the cornea being too flat.

In astigmatism, the cornea, or window of the eye, has an irregular curvature being shaped more like a rugby ball, rather than a soccer ball. Light rays are focused at different points. A person often has some degree of astigmatism and myopia or hyperopia at the same time.

In myopia laser correction procedures, the cornea is flattened to better focus light rays normally on the retina, whereas in hyperopia, the cornea is made more curved. With astigmatism, the surface of the cornea is re-sculptured to a regular curvature.

Under one method of treatment, known as photorefractive keratectomy (PRK), the, laser beam is applied directly to the surface of the cornea, after the thin surface layer of epithelium cells has been removed (e.g., through solvent with wiping, preliminary laser treatment, or minor abrasion). After the direct laser re-sculpturing of the cornea, a bare area of the cornea is left which takes a few days to heal (e.g., 2 to 6 days) and can be uncomfortable during this period. The healing process can sometimes lead to regression (some refractive error returns) or to scarring (which may blur the vision), especially in patients with large refractive errors. Although still used for low degrees of myopia and hyperopia, PRK is generally being replaced by the LASIK method for these same disorders, in which the laser treatment is applied under a protective corneal flap. Under the "Laser in situ Keratomileusis" (LASIK) treatment, a thin protective corneal flap is raised, rather like a trapdoor. The front surface of the exposed cornea is treated by the excimer laser. The net result being that the cornea is altered in a manner directed at allowing light rays to be focused normally on the retina. At the end of the procedure, the protective flap is simply replaced. The LASIK technique leaves the original surface of the cornea virtually intact, hence, there is no bare area to cause pain. In addition, the mild healing process results in minimal regression and avoids scarring problems.

Presbyopia is a problem that is due to an aging process occurring in the natural lens of the eye, and thus is not linked to the cornea being incorrectly shaped as in myopia, hyperopia and astigmatism. As a person ages, the lens expands, becomes harder and less pliable and, because of these factors, is not as capable of changing its shape to focus. In a typical situation, once a person reaches about 40 years of age, the loss of elasticity and the expansion in the natural lens of the eye results in that person experiencing problems with focusing close, for example, during reading. Most people, as they age, suffer from a presbyopia problem. The usual way to correct this problem is to use bifocal lenses. However, some people dislike wearing glasses, particularly bifocals, for many reasons. For example, bifocal lenses present lines where the two portions of the lens are joined together and thus can be unsightly unless more expensive "no line" bifocals are relied upon. Furthermore, people must become accustomed to reading through the one relatively smaller portion of the bifocals.

Because of the underlying differences in the causes for presbyopia and the group of myopia, hyperopia and astigmatism, many ophthalmologists have concluded that there is no cure for presbyopia and that the only solution is to wear reading glasses to compensate for the loss of ability to focus on close objects.

Chapter 4 of the book *Surgery for Hyperopia and Presbyopia* of Neal A. Sher, M.D., F.A.C.S., 1997 (which book is incorporated by reference in its entirety), describes a corrective presbyopia surgical treatment known as of "Anterior Ciliary Sclerotomy" involving the placement of radial incisions over the ciliary body in an effort to increase the scleral diameter to provide an increased area for ciliary muscle action. This technique is based on the belief that it is not elastic loss in the lens, but a loss in range of action due to the lens' continued growth with respect to a non-growing sclera. The potential complications for this type of a treatment, such as infection, hemorrhage (from cutting to deep), ocular hypotension, myopic shift, and compromise of the limbal conjunctival barrier, makes this technique one that is unlikely to gain wide acceptance.

U.S. Pat. No. 5,314,422 to Nizzola represents one effort to correct presbyopia and involves remodeling, in a PRK process, the front or external surface of the cornea by applying a laser beam through two manipulated plates which together form a sickle shaped aperture. The beam passing through the aperture forms a corresponding sickle shaped recess in an area situated in proximity to the lower part of the pupil rim. The remodeled area thus constitutes a zone of the cornea which functions differently than the rest of the cornea. Thus, this technique simulates a bifocal glasses arrangement and therefore presents the problem of having to shift ones focus from one area to the other depending on the desired viewing object. Also, the technique described in the Nizzola patent is a PRK procedure which removes portions of the outer epithelium layer of the eye and exposed surface of the cornea therebelow and, as a result, complicates and prolongs the healing process which healing process can sometimes lead to scarring and is often uncomfortable to the patient.

Chapter 20 of the aforementioned *Surgery for Hyperopia and Presbyopia* describes a small diameter intracorneal inlay lens technique used in an effort to correct presbyopia. Under this technique, an incision is made in the eye and a small spatula is utilized to dissect a pocket to the center of the cornea. A small (1.8–2.2 mm diameter) intracorneal hydrogel inlay lens is then placed on the spatula and centered over the patient's pupil. This technique is described as providing a multifocal cornea arrangement. However, this technique is relatively invasive which brings with it the possibility of scarring and infection, and the introduction of a foreign body into the eye is sometimes found unacceptable by some patients.

Chapter 7 of the aforementioned *Surgery for Hyperopia and Presbyopia* also features a PRK type presbyopia treatment discussion which is directed at creating a defined bifocal or multifocal surface of the human cornea relying on the pseudo-accommodation ability of the patient to be effective. In the PRK treatment described in Chapter 7, a 193 mm excimer laser (MEL 60 Aesculap Meditec, Heroldsbery, Germany) is used. The techniques described include a straight PRK presbyopia treatment, a combination myopic/presbyopic PRK treatment and a combination hyperopic/presbyopic PRK treatment which include rotating and stationary masks designed to form the desired bifocal or multifocal cornea surface topography on the exterior of the cornea with heavy emphasis on a sectorial corneal profiling or on a semilunar cornea steepening profiling to achieve in a defined part of the cornea a presbyopic optical correction. Thus, in some ways this technique is similar to that of the Nizzola method described in U.S. Pat. No. 5,314,422 for presbyopia treatment and thus shares common problems with the Nizzola technique. Additional complications include monocular diplopia and the loss of visual acuity which resulted in some of the clinical tests reported.

Yet another, example of a PRK presbyopia treatment process can be seen in U.S. Pat. No. 5,395,356 which describes a PRK reprofiling of the cornea to create at least one "add" region having a different focal point in an effort to assist the eye in accommodating close-viewing conditions. The "add" region is described as preferably being located near the center of the optical zone and is formed by ablating a profile in Bowman's membrane or Bowman's membrane and adjacent upper portions of the stroma following removal of the outer epithelium layer in a preliminary laser application. As described above, the PRK treatment process, because it leaves exposed ablated areas in the cornea, has associated with it an uncomfortable healing process and the potential for scarring, hazing and infections.

Section IV of the *Surgery for Hyperopia and Presbyopia* book noted above provides a discussion of an automated lamellar keratotomy (ALK) for hyperopia and laser in situ keratomileusis (LASIK) for correcting hyperopia (Chapters 12 and 13) each of which involves the formation of a corneal flap. As described in Chapter 12, through the work of the present inventor, following upon the earlier work of Dr. Jose Barraquer, nomograms for the correction of hyperopia have been developed for causing a controlled degree of ectasia in the eye to produce a hyperopia correcting steepening of the cornea. The controlled degree of ectasia is based on precise lamellar flap formation which, as described in Chap. 12, preferably involves controlled flap formation through the use of an automated microkeratome such as that described in U.S. Pat. No. 5,133,726 to the present inventor and Sergio Lenchig, which patent is incorporated herein by reference.

The above noted Chapter 13 describes a hyperopia correction procedure, which involves ablating with an excimer laser cornea tissue underlying a displaced lamellar corneal flap formed with a microkeratome like that described above. Following flap formation, a hyperopia correcting mask is attached to an eye fixation suction ring through use of a Meditec handpiece and mask support system. The shape of the mask is dependent on the hyperopia refractive error being corrected, and the laser system directs a sweeping laser beam past the mask which rotates through 360°, with adjustable speed (e.g., an angular increment following each laser beam sweep across the mask). Reference is also made in this Chapter to the earlier work of others in the use of LASIK in the treatment of myopia. In this regard, reference is also made to U.S. Pat. No. 4,903,695 to Muller and L'Esperance describing the treatment of myopia, hyperopia and astigmatism through the use of a laser applied to a freshly cut part of the cornea after severing of the lenticle.

Some efforts have also been made to avoid the need for presbyopia correction glasses by programming a laser's computer to leave one eye slightly myopic after treatment, with the other programmed for distance. This is sometimes referred to a monovision, and is often done with patients being subject to a conventional LASIK treatment. However, while helping to avoid the requirement of reading glasses in some patients, a monovision treatment requires some deviation from the desired approximation of normal vision and thus represents a determination that the monoscopic state is not as undesirable as having to use reading glasses. While a minor degree of a monoscopic vision procedure may be useful in supplementing a presbyopia treatment, sole reliance on monovision for correcting presbyopia, however, is undesirable due to the resultant wide variance from normal vision parameters.

The aforementioned U.S. Pat. No. 5,533,997 to the present inventor describes a presbyopic treatment method and system that includes, in one embodiment, a system and treatment method preferably involving flap formation and the controlled formation of an annular ablation in a centralized region of the newly exposed corneal stroma so as to produce an unablated central protrusion of the stroma which transforms the exterior surface of the replaced flap into a multifocal surface that is effective in providing both good near and far sight and is thus effective in avoiding the difficulties imposed by the onset of presbyopia.

As described in U.S. Pat. No. 5,533,997, a preferred treatment technique is one wherein the ablation zone leaves untouched a central corneal area of preferably 1–3 mm and provides a presbyopic corrective ablation ring which has its major depth region also in a relatively central region of the cornea (e.g., a 3.5 mm outer periphery for the presbyopic correcting depth with or without outward additional smoothing). As described in the above referenced application of the inventor, there has been noticed by the inventor that the occlusion of about a 3 mm central area of the cornea does not affect far vision, which led to the realization by the inventor that this is an ideal site for the near vision correction by means of reshaping this zone with a multifocal shape and leaving the most peripheric area of the cornea for intermediate and far vision. In an effort to even further improve upon this earlier work in presbyopic correction in categories such as facilitating laser parameter determination and setup time from patient to patient, helping to avoid mistakes in the setup, and application of an ablation profile well suited for a patient to be treated, hastened healing time, minimizing the degree of postoperative regression, avoiding undesirable reflection or glaring, and generally providing a good near and far vision relationship in the treated eye(s), further study and clinical testing has been carried out with the result being a presbyopic treatment system and technique as described below.

SUMMARY OF THE INVENTION

The present invention represents a building upon and refinement of the presbyopic treatment system and technique described in parent applications U.S. Ser. No. 08/268,182, filed Jun. 29, 1994 (now U.S. Pat. No. 5,533,997) and U.S. Ser. No. 08/660,376 filed Jun. 7, 1996 (now U.S. Pat. No. 5,928,129). In the two parent applications, there is described a process and system for correcting presbyopia carried out either alone or in combination with the correction of one or more refractive corrections such as hyperopia, myopia and astigmatism, which preferably involves reshaping an eye to as close as normal vision warranted under the situation, and then making a presbyopic correction in accordance with the procedure set forth in those parent applications. As in the parent applications, the present invention preferably involves a process that includes anesthetizing a patient and marking a portion of an eye of the patient which is to be ablated, which is followed by the resecting of at least a portion of the cornea to expose the corneal stroma. An annular portion of the corneal stroma is then ablated using radiation from, for example, a laser beam. After ablation, the cornea is repositioned onto the eye.

In a preferred process of both the parent applications and of the present invention, the cornea is resected such that a portion of the cornea remains intact, and thereafter, the cornea is folded back to expose the corneal stroma. Alternatively, the cornea may be resected such that a complete disk of the cornea is removed from the eye, to thereby expose the corneal stroma. Thereafter, the cornea disk would have to be reattached onto the eye.

The corneal stroma should be dried after it has been exposed by the resection and before the ablation process. Otherwise, uneven ablation may occur due to liquids present on the stroma.

In accordance with the present invention, there is provided presbyopic corrective contour control means for forming, in the exposed corneal stroma following flap formation, an annular presbyopic correction contour based on a predetermined profile. This control means is preferably used in association with a laser generation means such as an excimer laser, although other suitable corneal stroma removal techniques may also be relied upon (e.g., a fluid jet or mechanical material removing device). The control means of the present invention includes presbyopic corrective directive means which preferably is in the form of a programmed software or hardware application such as a software or hardware module or component which represents either the entire programmed control system of a laser system or an added and modifying; component or portion of a larger programmed laser control system. In a preferred embodiment, the tissue removal directive means is a software or hardware component that is added to a conventional or preexisting laser system which preferably includes an eye tracking feature for added assurance of proper profile formation in the exposed corneal stroma.

One example of a preexisting laser system which can be modified for use in the present invention, includes the aforementioned MEL60 193 argon fluoride excimer laser of Aesculap-Meditec. An additional example includes the VISX Star Laser System of VISX Inc. (Santa Clara, Calif.) which features a dual diaphragm system for the treatment of myopia and myopic astigmatism and a hyperopic module that is added along the laser passageway for hyperopic treatment. The delivery of the excimer laser energy in the Star System is carried out using a computer-controlled delivery system which relies on its VisionKey software system, with its WORM (write once read many) optical memory card for enabling the system operator to program the specific refraction corrections for each patient. Through suitable modification or supplementation of the computer-controlled delivery system of the VISX Star System in accordance with the parameters and other features set forth below (which can be seen, for example, to include unique input values or ranges and one or more information transducers or converters for use in a unique profile or contour with such a cross-sectional profile determination technique), a modified VISX Star System can be formed that represents a suitable laser system of the present invention for carrying out the presbyopic profile contour formation procedure of the present invention described in greater detail below. Reference is also made to U.S. Pat. Nos. 5,163,934 and 5,207,668 issued to VISX, Inc., which patents are incorporated herein by reference. Reference is also made to U.S. Pat. Nos. 4,718,418 and 4,729,372 to L'Esperance (a listed inventor in one of the VISX, Inc. patents referenced immediately above) for further examples of ablation techniques that can be modified for use in carrying out the present invention. These '418 and '372 patents are also incorporated herein by reference.

As a further example of a preexisting laser system suited for modification to achieve the benefits of the present invention, reference is made to the Chiron-Technolas Keracor 117 and 217 laser systems of Chiron-Technolas GmbH with the laser systems being described as suited for myopia, hyperopia and astigmatism treatment through a computer-controlled movable mirror with relatively large beam scanning capability. The Chiron Vision's systems are also described as being suited for receiving software module updates for varying the system's preexisting suitable energy calculation and delivery parameters of the laser beam. This system also represents one system having an eye tracking feature. Thus, with an appropriate software module modification and/or addition carried out to achieve the parameters and features of the present invention, the Chiron Vision system can also provide a laser system suitable for modification in accordance with the present invention.

Another example of a laser system that can be modified for use in carrying out the beneficial features of the present invention can be seen in the Summit Technology, Inc.'s SVS Apex plus with mask in rail technology, and in U.S. Pat. Nos. 4,856,513; 5,019,074; 5,324,281; 5,395,356 and 5,651,784, all to that same company, which patents describe various means for forming laser sculptured configurations including the use of erodible masks that are disposed between the laser and the cornea for providing a predefined profile of resistance to erosion so as to form a desired laser erosion in the eye. These five patents to Summit Technology Inc., are incorporated herein by reference. Through use of the present invention's specified parameters for correcting presbyopia (alone or in combination with one or more refractive correction procedures for myopia, hyperopia and astigmatism) in the central region of an exposed corneal stroma surface, a suitable erodible mask member can be formed for use in forming the desired presbyopia correcting parameters of the present invention.

The "LSX" laser system of the LASERSIGHT Corporation in Orlando, Fla., US, in combination with the preferred parameters of the present invention and the LASERSIGHT Corp.'s "Scanlink" software system, provides another suitable laser system in accordance with the present invention. The Scanlink System provides a translation process that can be used in the ultimate directing of the laser system's "flying spot" laser beam to contour the desired profile. Under the present invention, this can include setting parameters within reception areas of a modified version of this software based on, for example, certain measured values that can vary from patient to patient (e.g., the limbus to limbus length, measured corneal curvature, etc.) and/or desired values chosen from a plurality of parameter reference representative point ranges. The input values are preferably inputted into reception areas which can be fields that appear on a computer monitor screen including representations of values within a range which can be mouse-clicked upon to choose a desired value within a range appearing in the particular fields presented. The "LSX" system also includes an eye tracking system and can provide the desired ablation profile within, for example, 20 to 30 seconds, which is useful in carrying out the method of the present invention and is preferably an added structural component of a preferred ablation system.

For ease in usage, it is preferred that any laser control system of the present invention has provided with it associated hardware and/or software which includes the advantageous presbyopia correcting profile parameters of the present invention such that the operator need only input a few reference points that can be easily measured in the patient and/or chosen from representative choices, whereupon the inputted data concerning the patient is automatically processed to produce the desired profile or contour configuration for determining the resculptured corneal stroma configuration. It is also preferable to provide a visual display of the two dimensional ablation profile and/or a two or three dimensional representation of the final contour to be provided in the corneal stroma for, for example, pre-laser system operation review by the operator. Thus, through the use of hardware or software or the like, automatic profile configuration means is provided under the present invention with the profile shape having a configuration that is in accordance with the present invention's parameters (e.g., a representative single general profile equation) as discussed below.

Although less preferable from the standpoint of operator complexity, the present invention can include a laser control system having hardware or software designed to accept on each time of use inputted data which includes the present invention's profile determining means parameters (e.g., an inserted additional software, module or disk, or other data input means) to be read by compatible additional software or hardware already stored by a processor of the laser system's control system. This additional inputted data therefore preferably includes, together with the data related to variable measurements, data and means for determining the desired profile configuration for that patient. The inputted measurement data and the predetermined profile configuration parameters in accordance with the present invention, can either be analyzed by the control system's receiving hardware or software or combined by the inputted data means prior to receipt by the laser control system's hardware or software. An example of this latter embodiment can include, for example, inputting a series of points from a drawn or hard copy of a profile or a profile reception tablet in conjunction with a pick up instrument (e.g., a digitized tablet in which, a profile can be inputted and which either forwards upon acceptance confirmation the digitized profile directly to the control system of the laser or which involves the scanning of a depicted resultant profile by another instrument linked to the control system such as a digital scanning pen)

Further examples of systems which can form a basis for modification to achieve the beneficial features of the present invention can be seen in the solid state, computer directed "flying spot" Novatec "Light Blade" UV photoablation laser described in Chapter 11 of the above noted *Surgery For Hyperopia and Presbyopia* as well as the Nidek EC 5000 laser described in Chapter 10 of that same book. In Chapter 10 of that book, the Nidek EC 5000 laser operators are described as contemplating using an in-house algorithm for initial software correction in an effort to input an overcorrection feature in the system.

As can be seen above, a wide variety of laser sculpting systems exist such as ones using focused direct laser beam applications (e.g., flying spot), and wider beam applications with blocking or masking means such as erodible masks or rotating and/or stationary single or multi-holed plates, etc., and these systems can be used as a basis for carrying out the present invention upon making the appropriate modifications in accordance with the features of the present invention.

In addition to the above described means for ablating a corneal stroma and means for resecting at least a portion of the cornea of the eye, the system of the present invention also preferably includes a means for marking a portion of an eye of a patient to be ablated.

The present invention also preferably includes means for designating or referencing a desired central point for a central unablated zone used in forming a multifocal presbyopic corrective corneal contour. This central point designation or referencing arises from the inventor's determination that it is beneficial to position the central point of the central area to remain free of ablation one unit superior and one unit nasal to the center point of a patient's pupil. The unit length is determined by separating the pupil into quadrants by way of crossing horizontal and vertical intersecting lines and dividing the nasal and superior radial lines into thirds and marking, or designating a spot which represents the crossing point of line extensions of each of the ⅓ dividing points within the nasal/superior quadrant that are closest to the pupil's center. This can be done automatically with an appropriate information transducer or converter of a central system through an input of a patient's pupil width or by input from a pupil measuring means. As an example, a 2 mm pupil would have a desired central point for the unablated area 0.33 mm closer to the nose and 0.3 mm superior.

The system also preferably includes means for drying the corneal stroma after it has been exposed by the means for resecting such as an air blower with filter system. Thus, once the cornea portion has been properly repositioned, it may be reattached to the eye by blowing air onto the cornea.

An additional feature of a preferred embodiment of the present invention includes a means for cleaning the portion of the stroma that was ablated. This means may include a delicate brush and/or a means for irrigating the portion that was ablated. That is, after ablating, the ablated portion should be cleaned, in order to prevent edema and this may be accomplished by brushing and irrigating the portion which was ablated.

In one embodiment of the present invention, in order to ablate the corneal stroma in an annular fashion, a mask formed of a synthetic resin such as polymethyl methacrylate (PMMA) can be utilized. The mask in conjunction with a suitable laser power, shape and position system (e.g., a fixed diameter sizing feature which, together with the smaller diameter mask) forms together a means for maintaining the central area protected while forming an annular presbyopia correcting main zone in the corneal stroma. This arrangement is useful in forming a basic presbyopia correction profile which can be refined to lessen, for example, the post operative time required for some undesirable eye conditions to clear up.

BRIEF DESCRIPTION OF THE DRAWINGS

The invention will be described in more detail with the aid of the attached drawings, wherein:

FIGS. 5A–5D show representative examples of a variety of profiles which represent the predecessors leading up to the profile depicted in FIG. 4A;

FIG. 5E represents another view of the ablation profile representation of FIG. 4A and which presents an illustrative view of what can appear on a visual screen or the like associated with a laser control system;

FIG. 6 shows a schematic view of another embodiment of a presbyopia correction system with presbyopia corrective contour control means forming part of the overall presbyopia correction system.

DETAILED DESCRIPTION OF THE INVENTION

Figure 1:
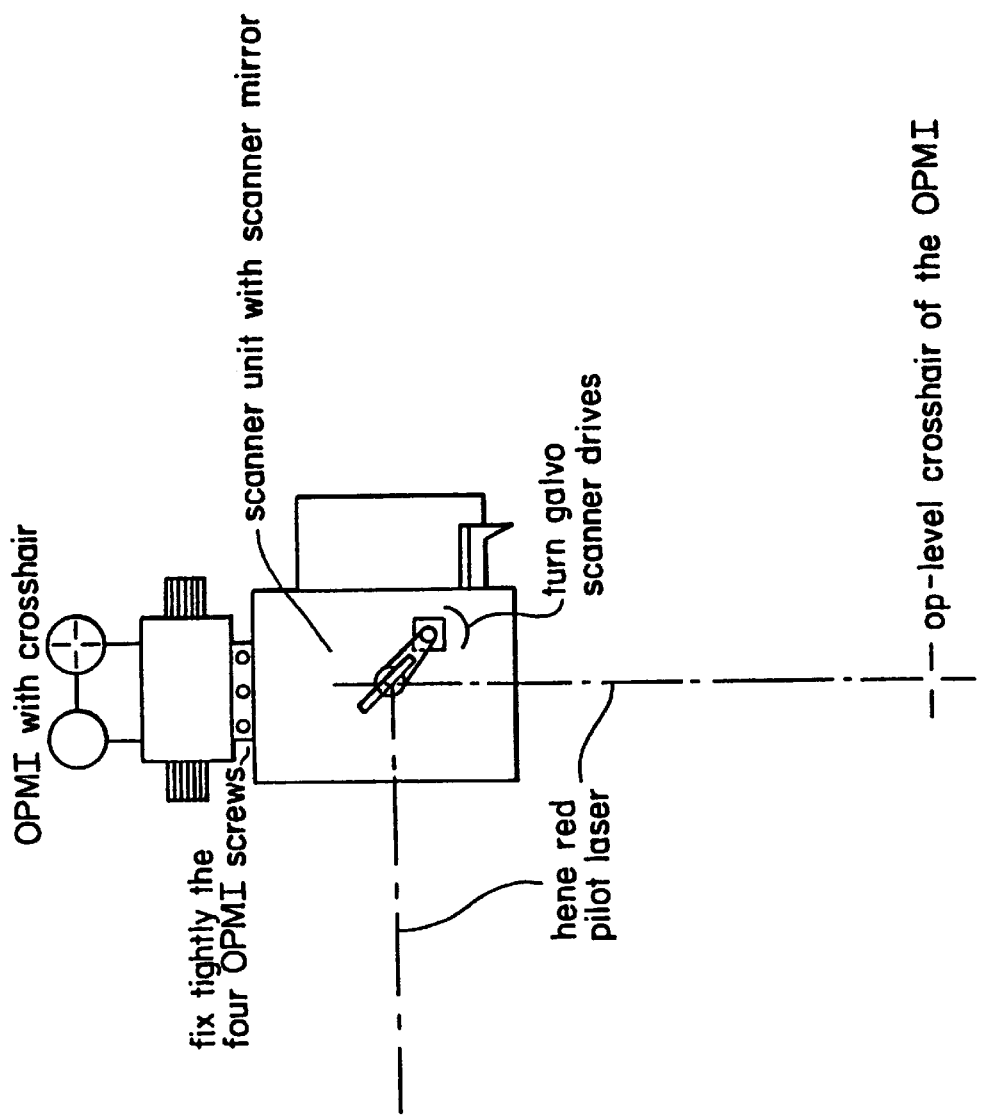
FIG. 1 is a schematic view of a portion of one excimer laser system where the setting of the axis of the laser ray is performed.

A system in accordance with the invention includes a corneal stroma material removal system (e.g., an excimer laser system) with presbyopic corrective contour control means, an automatic corneal shaper, a pneumatic fixation ring, a mask and an air source. A preferred automatic corneal shaper for use in the system in accordance with this invention is the Automatic Corneal Shaper described in the inventor's U.S. Pat. No. 5,133,726, issued on Jul. 28, 1992. This patent is entirely incorporated herein by reference.

Using only a local anesthesia, the eye is fixed by the fixation ring which also functions as a guide for the automatic corneal shaper. The fixation or retaining ring, as illustrated in the above mentioned U.S. Pat. No. 5,133,726, permits total control of the eye movement. The pupil of the eye will be a reference point for making a very central stromal ablation on the cornea or some other suitable reference point can be used such as the vision axis or nasal-superior center point described in greater detail below with respect to the laser system zones.

Once the eye is fixed, a keratectomy is performed using the automatic corneal shaper. The keratectomy may be partial, which means that a cornea flap technique is used. This means that an end portion of the corneal disc remains attached to the cornea base, which thereby permits its repositioning in an easier and surer way, once the ablation is performed. When the flap is retracted, the corneal stroma becomes exposed, which is ideal tissue on which to practice the ablation. The superficial layers of the cornea remain untouched. In this way, undesirable healing is avoided, and inaccuracy in the post operative correction and regression is also avoided.

In one embodiment, an excimer laser system is used with presbyopic corrective control means, which, preferably, features a controllable excimer laser that accurately allows an ablation of 0.24 μm/pulse such that an annular ablation can be made on the stroma having a presbyopic corrected external diameter of about 3.5 mm or less (with or without additional exterior and interior smoothing), with a central zone as small as 1 mm diameter and varying between 1 to 2 or 1 to 3 mm. The annular ablation produces a central protrusion of the stroma such that when the corneal flap is repositioned at its initial position, this stromal curvature change is transmitted to the forward corneal surface, thereby indirectly transforming the corneal surface into a multifocal surface, which is, in fact, myopic in its central part. This is what helps make it possible for the patient to read without optic correction after the procedure, regardless of the age of the patient or the loss of accommodation.

The annular ablation can be made in isolated form, for presbyopia correction, or it can be made together with hyperopia, myopia and astigmatism surgery, either isolated or combined. After the ablation is made, the procedure continues with exhaustive cleaning of the interface using a balanced saline solution, a brush and aspiration, in order to assure that the interface is free from impurities, epithelial cells or foreign particles. Thereafter, the flap is replaced in the bed, adequately oriented in order to avoid altering its natural position. The edges of the flap are dried using air for several seconds to obtain adherence of the flap, such that the patient may be permitted to leave the operating room with no bandages and to obtain less than 24 hours recovery time.

The surgical procedure in accordance with the invention should be carried out in a sterile area (i.e., a surgery room), because the cornea will be touched not in a superficial manner as would be required for a PRK photo-ablation for the correction of myopia. Rather, in the presbyopia corrective surgical techique in accordance with the invention, a corneal flap is lifted in a laminar way in order to work directly on the stroma. Therefore, surgical fields are located in order to isolate the working area and also a blepharostat is provided in order to maintain the eye sufficiently exposed so as to be able to practice the surgery.

A marker is advantageously used to aid in the practice of the invention. The marker used in this new technique has the shape of a bullock eye having two concentric circles (thereby forming an inner ring and an outer ring) in which its external portion has a diameter of about 10.5 mm and its inner part, in one embodiment of the invention, has a diameter of about 3 to 5 mm. This marker is impregnated with a coloring product, such as gentian violet, methylene blue, or the like. The marker is placed on the patient's eye. The internal ring has the function of centering the marker, having as a reference point, the pupil or a previously marked or determined reference location. In this manner, the external ring is automatically marked and in turn this will be used as a reference when positioning of the pneumatic fixation ring. In addition to these two rings, the marker also has a para-radial line joining both rings. The para-radial lines are useful for adequately orienting the corneal flap. Alternatively, in the case where a completely separated corneal disk is removed for the surgical procedure instead of using a corneal flap, the para-radial lines are used in order to assist in positioning the disk in the right place, that is, epithelial toward the exterior and stroma toward the inner part, and once located in this manner, it may now be oriented in adequate form.

The pneumatic fixation ring comprises two main components. The ring itself which will be adapted to the eye by means of a bottom vacuum chamber, allowing it in this manner to hold the eye in place and to increase the intra ocular pressure. This makes it easier to make the necessary cut in the cornea in a uniform manner. The fixation ring also has a central orifice through which the cornea protrudes. In its top portion, there is provided on the fixation ring a line of toothed protrusions which contact with the pinions of the automatic corneal shaper (see U.S. Pat. No. 5,133,726). This allows the corneal shaper to be displaced in a horizontal way for performing the laminar cut in the cornea. The second component of this ring is a handle which places the bottom vacuum chamber of the fixation ring in communication with a vacuum pump. The vacuum pump is responsible for suction fitting the ring on the patient's eye. This handle also is used to manipulate the eye once the ring is fixed to the eye.

The next step of the surgical procedure is performed by the automatic corneal shaper, as noted above. The shaper is positioned over the fixation ring, and once the pinions of the shaper are in contact with the toothed protrusions of the ring, the shaper motor is started, and the shaper is moved horizontally and uniformly over the cornea. The cutter of the shaper will make the laminar cut very accurately in its thickness, in the manner described in U.S. Pat. No. 5,133,726.

Preferably, the motor of the shaper is stopped at a predetermined position of the cut so as to have a thin portion of cornea still fixed to one side. When this thin portion is lifted, the corneal stroma will appear. The corneal stroma is the place where the object of the surgery will be practiced, because it has the great advantage that once the corneal flap is repositioned after the stromal ablation, all the natural structures of the eye will be preserved in their original place, but with a change in topography, thereby avoiding unwanted healings and other alterations that would be present if this system is not used. As an alternative, microkeratome to that described in U.S. Pat. No. 5,133,726, reference is made to Chiron Vision's *Hansatome Microkeratome* for forming the corneal flap.

Once the exposed stromal surface is examined, it must be dried prior to the ablation action of an excimer laser, because any remaining fluid on the stroma will be considered by the laser ray as corneal tissue. This would result in an irregular ablation; that is, different depths of ablation would be produced on the stroma.

Figure 2:
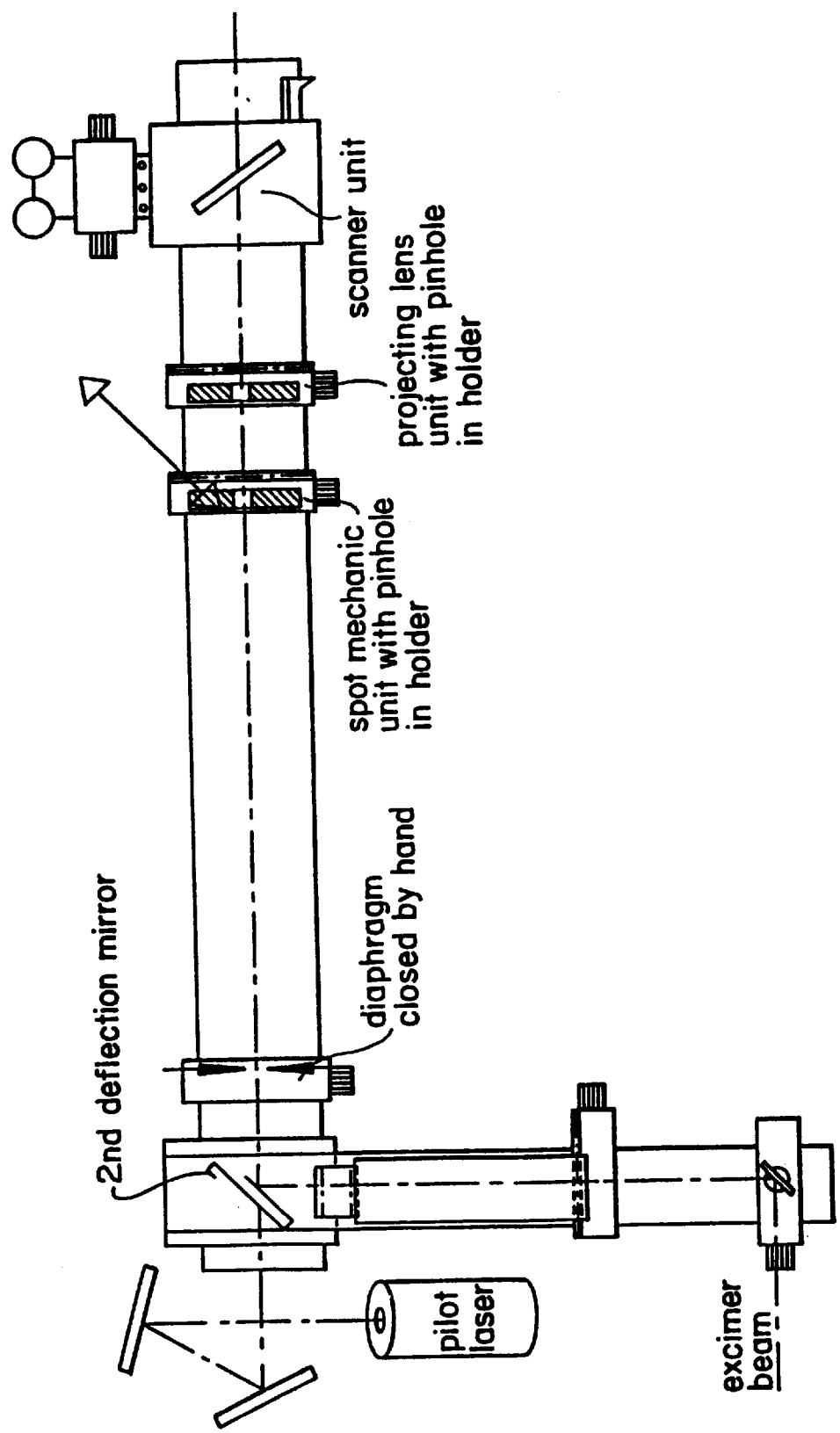
FIG. 2 is a schematic view of the path of the laser beam and the optics used in the laser system embodiment of FIG. 1.

One main element of a preferred embodiment of the system for the correction of presbyopia, is an excimer laser system, in view of its ability to accurately ablate a desired profile. One embodiment of an excimer laser system is illustrated in FIGS. 1 and 2, and the illustrated embodiment is one that will perform the correction of this visual defect by providing a stromal ablation in the required manner with respect to location and depth in order to create a multifocal surface in the cornea that allows good far sight, as well as good near sight. This good near sight of a person is usually lost during a person's later years due to a presbyopic physical lack of accommodation due to, for example, loss of elasticity of the lens.

The system of the present invention includes the novel combination of the above elements in order to obtain an annular shaped ablation within a corneal area which is not used for far sight. These are the theoretical and real bases of the system in accordance with the invention for presbyopia correction. There can be different ways to obtain the results, as will be described below.

In one embodiment, the laser is directed toward a zone where the ablation must be done. The laser is directed with a circular movement of the laser beam (e.g., a flying spot system) so that the ablation is made with the required width and depth, to thereby obtain the desired change in curvature. The variation in depth can be achieved, for example, by adding or subtracting to the number of repeat circular motions and/or varying the energy levels from one circumferential track to the next. For this, the apparatus that sends the laser ray beam includes an eye follower system in order to follow any movement of the eye, so that an irregular ablation ring does not result.

Figure 3A:
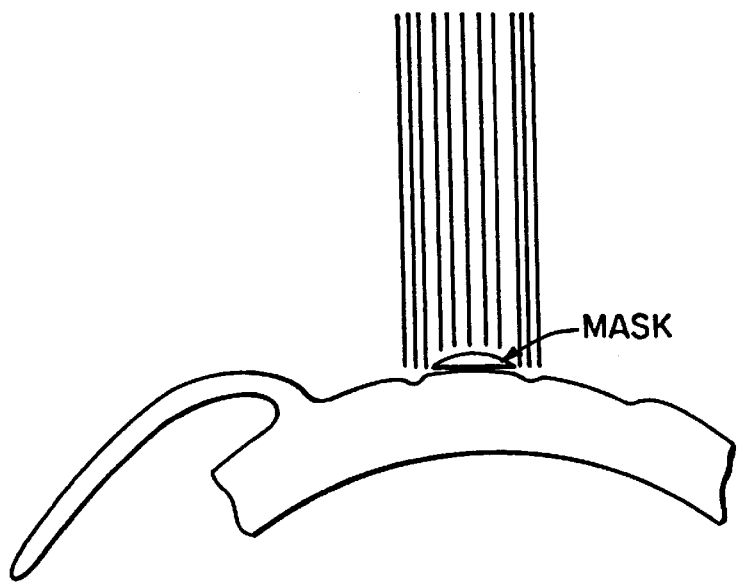
FIG. 3A shows the laser beam system performing an ablation on the cornea, and the mask protecting the center area of the cornea.
Figure 3B:
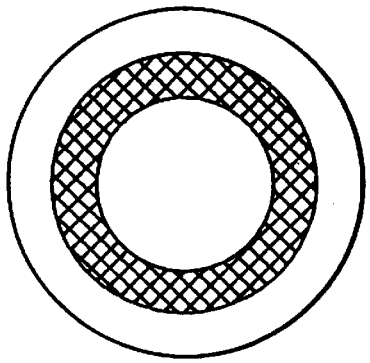
FIG. 3B shows the ring for the ablation zone.
Figure 3C:
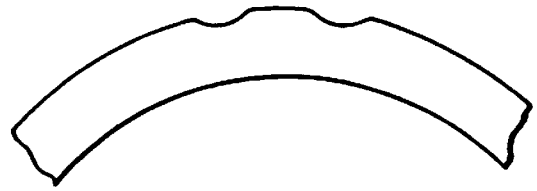
FIG. 3C shows the way the ablation of the cornea appears finally.

In another embodiment, as shown in FIG. 3A, the laser beam ray is sent toward the center of the chosen area, having as a reference point the center of a pupil, although other fixed reference points can be relied upon such as the nasal and superior unit shift described above and below. A mask is positioned over the central area so that it prevents the laser rays from touching the corneal stroma in the central area. In this manner, the ablation will be delimited at the outside by the selected diameter of the laser beam and at the inside by the border of the mask, thereby leaving a ring shaped area, as shown in FIGS. 3B and 3C. Using the mask, the cornea over the pupil area will be totally preserved.

With this in mind, one embodiment of the present invention's method for presbyopia correction proceeds in the following manner. Once the stroma is totally dried, the area that is not to be touched by the laser ray is marked. That area will be called the optic zone or "OZ" taking into account that one fundamental factor for the success of the operation lays on the centering of such optic zone. In one embodiment of the invention, the diameter of this optic zone can be as small as 1 mm, and preferably is between about 1 to 3 mm.

Over the marked area a mask can be provided made out of a material that stops the laser rays. For the mask, generally a material called polymethyl methacrylate (PMMA) is used, and it should have the same dimension of the mark already located.

The laser apparatus is then positioned so as to provide laser rays on the cornea. The laser apparatus is set in order to obtain a laser ray having the desired diameter. It also may be set up so as to provide a predetermined number of pulses which will be required for performing an ablation having an adequate depth so that the necessary corneal curvature change is produced, in order to obtain the multifocal effect. During the time of action of the laser ray over the cornea, and mainly when the laser equipment is not provided with an eye follower system, it is convenient to hold the eye with a pneumatic fixing ring in view of the fact that this permits a greater uniformity of the ablation ring produced.

Once the ablation step is completed, the mask is withdrawn, and the treated zone inspected and cleaned up completely, making sure that no epithelial cells or foreign particles remain, on the surface. The cleaning step is normally accomplished with a very delicate brush, with continuous irrigating using a balanced saline solution having an osmolarity similar to that of the cornea. This helps to avoid the induction of an important edema therein, which would cause a longer patient recovery time.

Now the treated surface is ready to receive the flap which has to be repositioned in its place, perfectly oriented and without folds that would cause induction of corneal astigmatism and reduction of the sight. Once the flap is repositioned, the tissue is dried by means of filtered air directed mainly to the borders thereof, to thereby obtain a good bonding of the flap to the treated surface. This bonding may be verified or tested with tweezers.

Once the tissues are bonded, the blepharostat and the surgical fields are withdrawn, and the patient is asked to blink their eyes several times and to close their eyes tightly, to further test the bonding of the tissues. If no complications are observed, the operation is now successfully ended.

FIGS. 4, 4A and 5A–5E are directed at a further refinement and improvement in the present invention which involves an improved presbyopic corrective profile that is preferably represented by a single equation (or direct or indirect derivatives or precursors of that equation) which profile governs or forms the basis for a preferred presbyopic corrective directive means. The presbyopic corrective directive means can take on a variety of forms or component parts such as software or hardware used in a laser system to control, for example, laser beam power, location and shape with respect to an exposed corneal stroma in either a direct corneal stroma application or in conjunction with a masking or blocking member, the adjustment and/or manufacture of a masking or blocking system to control what laser beam energy reaches the corneal stroma, the means for formation of an erodible mask and/or the erodible mask itself for controlled blocking of what laser energy reaches the exposed stroma, a supplemental feedback monitoring system that uses the equation or precursor or derivative thereof as the basis for a fixed or desired reference profile that the feedback monitoring system may rely upon in checking the progress of ablation, or any other control facet that is directly or indirectly related to the formation of a desired presbyopic profile contour in accordance with the present invention.

Figure 4:
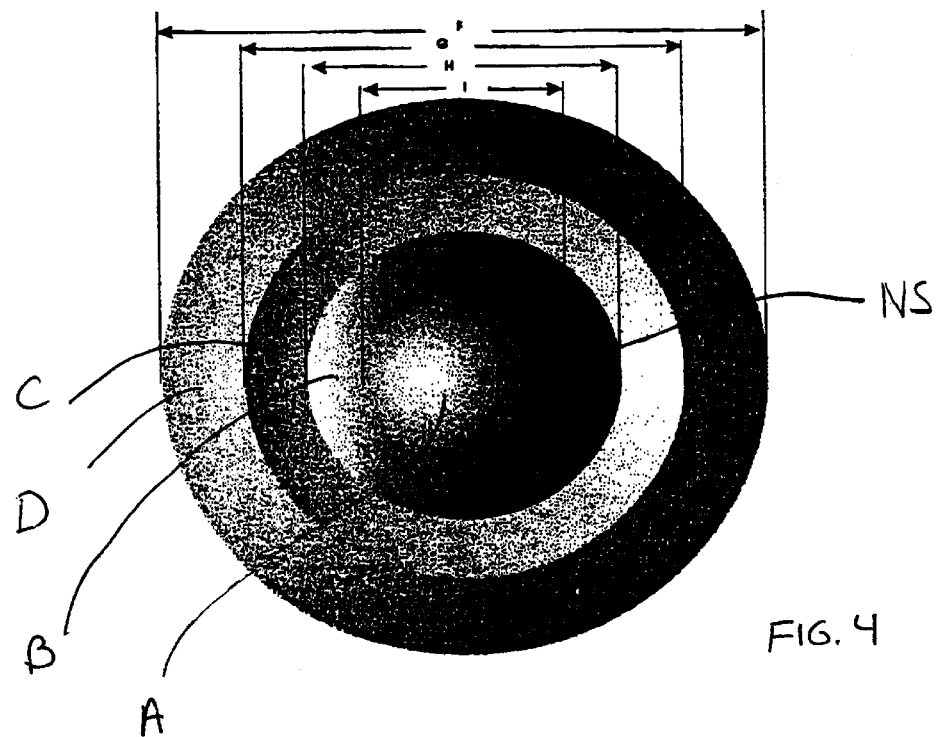
FIG. 4 shows a geometric circular zone illustration which is useful in the description of forming desired presbyopia correction profiles through ablation of certain volumes within specific illustrated zones.

FIG. 4 illustrates a geometric circular zone configuration which is useful in describing both the formation of the present invention's profile equation and the application of that equation in forming the basis for the presbyopic corrective directive means of the present invention. FIG. 4 is derived from the notion that the process for the correction of presbyopia is based upon changes induced on the corneal surface in relation to a visual axis of an eye, preferably by a laser system under specific ablation profile control. Such profiles can be defined by reference to the illustrated geometric circular zones and ablation volumes in these zones with predetermined specific characteristics. FIG. 4 illustrates four distinct zones with circular zone A being centered on the desired central point for the unablated area and having diameter I (mm). Inner annular zone B has outer diameter H (mm) and shares a common boundary with zone A and thus has an internal diameter I (mm). Intermediate annular zone C has an outer diameter of G (mm) and an internal boundary in common with the exterior boundary of B which is of length H (mm). Outer annular zone D has an internal diameter in common with the outer boundary of zone C of diameter G (mm) and an outer periphery having the illustrated diameter F(mm). The outer diameter is preferably taken from limbus to limbus which is typically about 10.5 mm.

Internal circular zone A, which is centered about a desired central point of the patient, as described below, and has diameter I (mm), represents the zone which is to be kept free of any laser activity by, for example, mask positioning or controlled avoidance of ablating laser contact within that zone. Zone B, with outer diameter H (mm), represents the maximum ablation (or removal) depth zone. Maximum ablation depth represents the corresponding correlation between diopters (i.e., 1/focal length,m) and the maximum depth of ablation of tissue in microns. Zone C represents the ablation perimeter limit that covers all of the ablation treatment zone. The outermost periphery of zone D of diameter F is represented by the limbus to limbus diameter. Thus, to summarize the relevant definitions:

Internal Diameter: the specific circular area preferably at the visual axis, of (I) mm, in diameter, that is to be kept free of any laser activity.

Maximum Ablation Depth: the corresponding correlation between diopters and the maximum depth of the ablation of tissue in microns.

Maximum Ablation Depth Zone: the distance (H) mm, for the area of the maximum ablation depth.

Ablation Perimeter Limit: the distance (G) mm, that covers all the treatment zone.

Exposed Corneal Stroma Zone: the diameter (F) which represents the limbus-to-limbus diameter of the eye.

In arriving at a presbyopia correcting profile equation which can be used as a basis for determining an advantageous, final presbyopia correction profile, in accordance with the present invention, and which is useful for a wide latitude of different patients (i.e., a universal equation approach), the following precursor mathematical formulas are relied upon in the construction of surgical profiles in accordance with the present invention.

The base variable used as a starting point is "X", and it is a floating point of movement on a plane constraint that is limited by the following parameters.

Dist: The distance of a point of interest to the center of reference which is defined by:

$$dist = \sqrt{x^2 + y^2}$$

The equation for "X" for use in determining the curvature profile is as follows:

$$X = zd - (k_1 * d) - dist$$

Wherein zd represents the main ablation zone B alone and without consideration for the transition zone C; $k_1$ represents a coefficient that defines the internal distance I (mm) of zone A; d represents the modifying factor for I (mm) such that the final product defines I (mm) as the interior zone to be kept free of any laser activity. The factor d can change in correspondence with a change, for example, in laser spot size when using a laser spot ablation technique.

Taking the above into consideration the very basic equation in the determination of curvature profile is:

$$F(X) = X^5 * (ri/2 - X) * k_2$$

Where $k_2$ is a coefficient defined as:

$$k_2 = 1 * 10^{13} * diop^4 * (ri^2 - (zd/2)^2)$$

and ri is the initial ratio of curvature of the cornea.

The subsequent step in establishing the desired final curvature is achieved by introducing an additional element to reshape the initial curvature equation F(X) as follows:

$$G(X) = F(X) + F(X) * (k_3/10 + factor/k_3) * \arctan(factor - 1)$$

Where the variable factor is a curvature index that determines the external slope and $k_3$ is the last coefficient that gives the final balance to the equation.

Figure 4A:
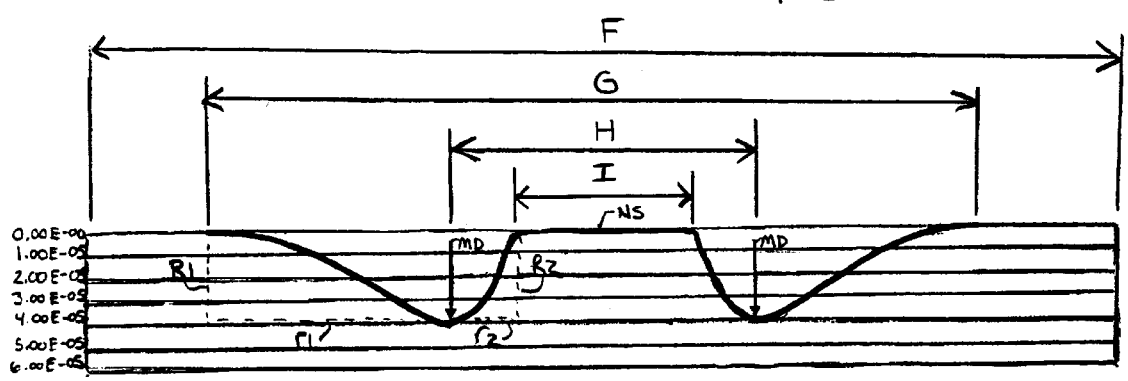
FIG. 4A illustrates a side view of one preferred ablation profile formed in accordance with desired parameters of the invention which is representative of a single profile equation, which profile equation is useful in forming presbyopic corrective directive means for determining the final corrective contour based on input patient data and, preferably, a choice or values within a plurality of range parameters.

The foregoing equation is a source for profiles such as the one represented in side view by the graph illustration in FIG. 4A which represents a preferred general profile configuration of the present invention for a typical presbyopia affected eye. As can be seen upon a 360° rotation of the planar profile in FIG. 4A, the corneal stroma will leave a centralized unablated zone, followed by a direct drop off with the transition between the central zone and sharp drop off preferably having a small radiused edge to a point of maximum deflection followed by a continuously smoothly curving extension in zone C which extends back to an internal boundary of an unablated outer zone D (with a radiused transition edge as well).

As the profile shown in FIG. 4A illustrates the ablation level for the laser system, zone A is shown as a flat, horizontal line due to a zero ablation effect on that region. FIG. 4A shows at the peripheral edge of zone A having a radiused (convex) edge which leads into a relatively steep, slightly concave, drop off profile section which extends to the maximum ablation point MD of the profile. Out from the maximum ablation point, there extends a smoothly curving ablation profile portion that is less steep than the drop off profile section (i.e., an aspherical relationship wherein the inner MD and outer MD slopes do not correspond) and extends from the maximum ablation depth out to the outer perimeter of zone C. As shown by FIG. 4A, a straight line approximation of the slope differential between the profile section extending out from point MD and in toward point MD is represented by $R_1/r_1$ and $R_2/r_2$. Since depths $R_1 = R_2$, the ratio of slope difference can generally be said to be represented by $r_1/r_2$ or (G−I)/(H−I). Also, the profile section that is defined by the lower quarter depth sections of the inner curvature portion leading to the maximum ablation point and the outer curvature portion extending off from the maximum ablation point represent a concave, cup-shaped section within the lower quarter of depth region, with about a ⅓ of the area of that cup-shaped section being inward of a vertical line extending through the maximum ablation point and the remaining ⅔ of that area outward thereof. The remainder of the less steep curvature extending over the remaining ¾ of depth has a smooth convex configuration which blends into the unablated area extending outward from zone C.

In general association with the illustrated profile in FIG. 4A, the following shows the preferred values and ranges for the diameters F, G, H and I.

F=limbus to limbus determination (approximate 10.5 mm)

G=7.4 mm (preferred range of about 7.0 to 7.8 mm)

H=2.8 mm (preferred range of about 2.4–3.2 mm)

I=1.6 mm (preferred range of about 1.4–1.8 mm)

The maximum ablation depth for the preferred profile contour is about 38 microns and a preferred range of depth is about 34 to 42 microns.

Figure 7:
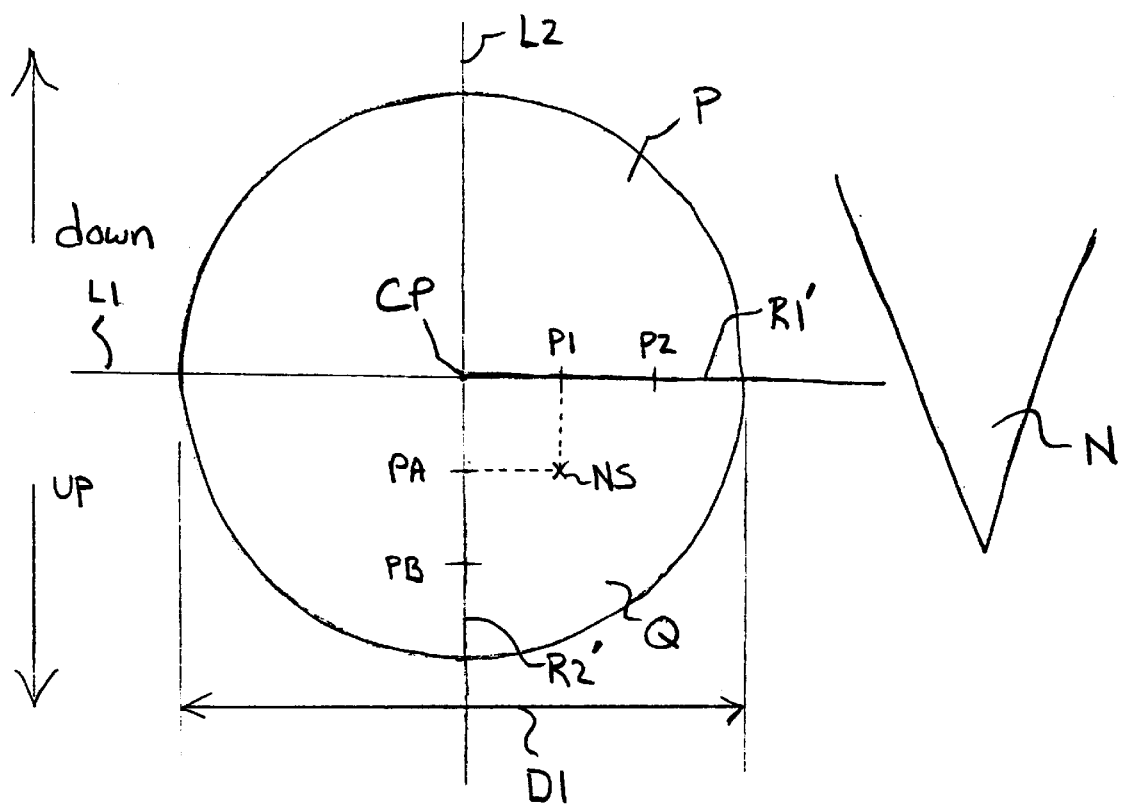
FIG. 7 shows a preferred central point for the non-ablated central region of the profile that is positioned nasal and superior to the center of the pupil.
Figure 4:
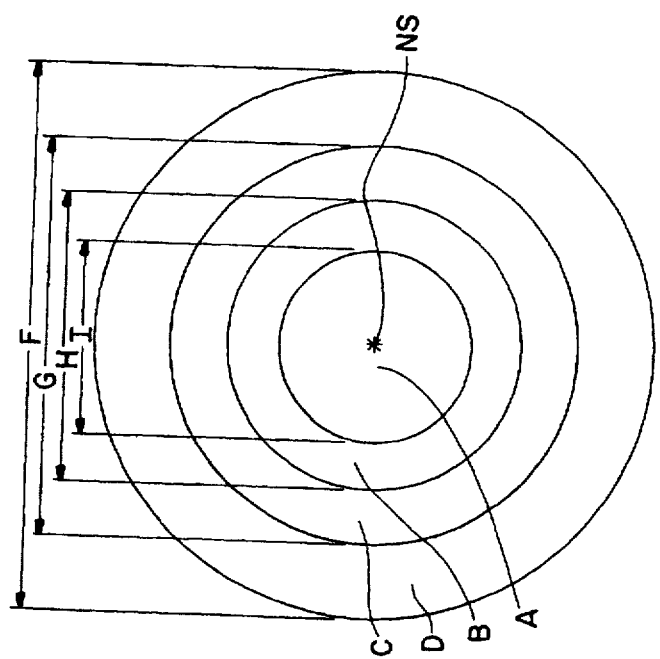
Figure 4A:
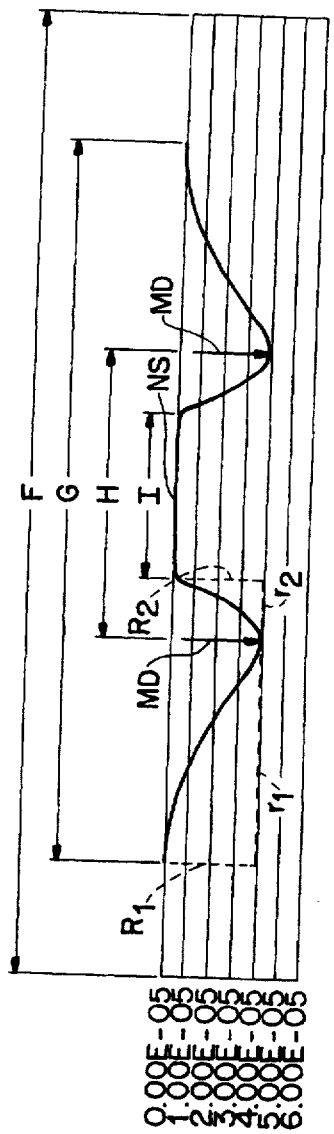
Figure 7:
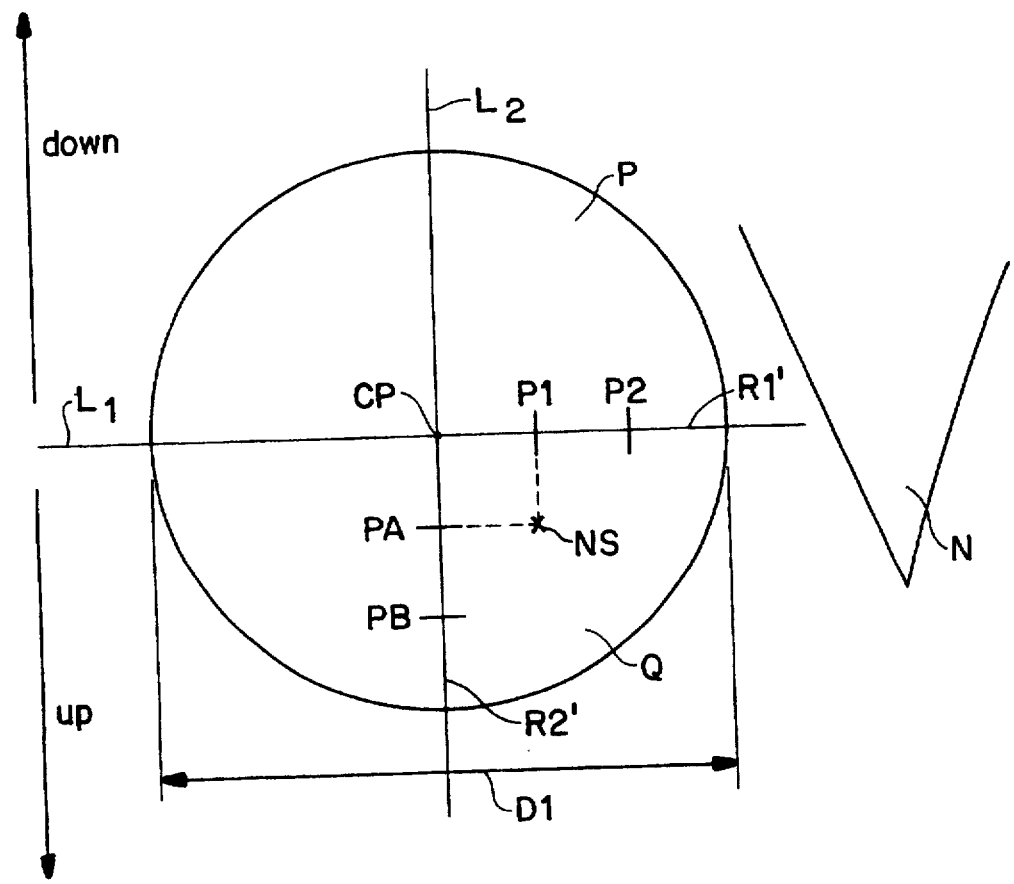
Figure 7:
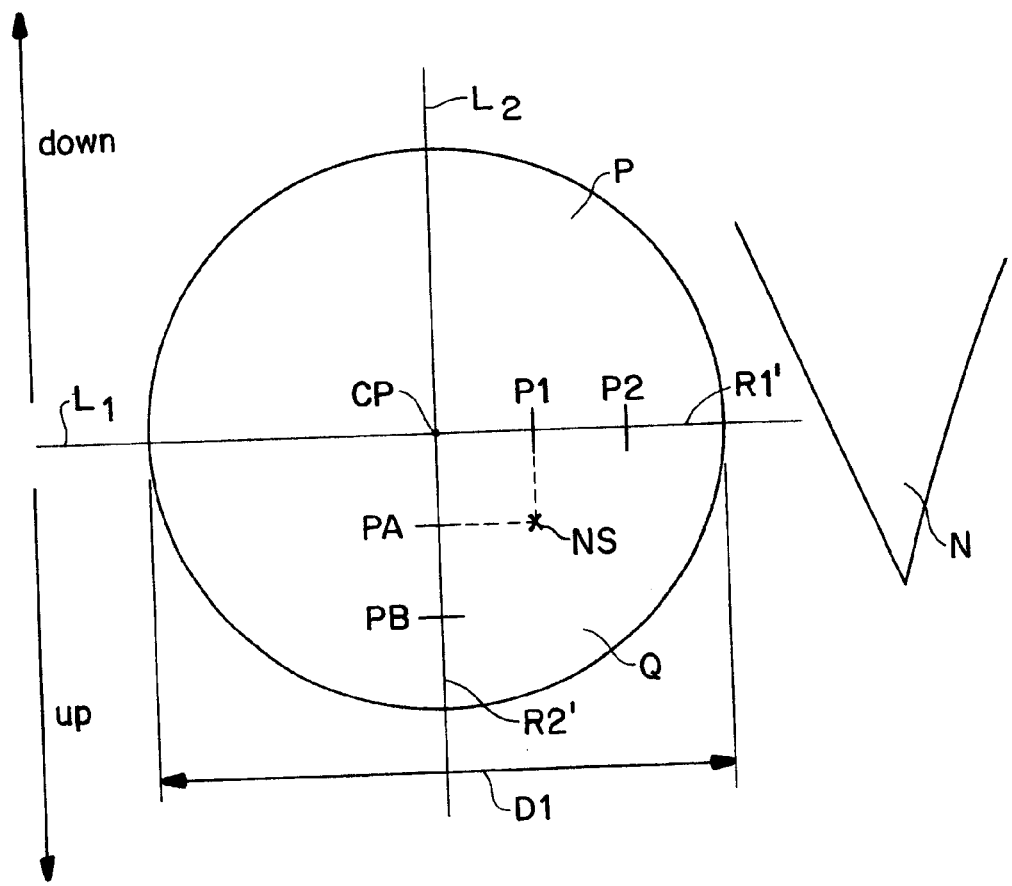

FIG. 7 provides a schematic illustration for determining a desired nasal-superior center NS point for the later-to-be-defined circular non-ablation zone A shown in FIG. 4. In FIG. 7 the left eye pupil P is shown schematically as well as nose N of the patent. The up and down arrows illustrate the superior and inferior half sections with horizontal line $L_1$ and vertical line $L_2$ passing through center point CP of pupil P. Lines $L_1$ and $L_2$ break up the pupil into four quadrants with quadrant Q representing the nasal-superior quadrant of the pupil. The radial lines R1' and R2' defining quadrant Q are divided into thirds by points P1, P2 and PA, PB. Nasal-superior point NS, which represents the center point for zone A, is defined by the intersection point for the lines extending from the points P1 and PA and into quadrant Q. Thus, for a typical pupil diameter D1 of about 2 mm, the unit length out to each of P1 and P2 is 0.33 mm. It has been found that this center point NS for the non-ablated zone is preferred in the presbyopia correction process. Suitable marking or tagging means of the desired NS point can be relied upon or reliance can be placed on a reference location system of a laser system alone.

To help illustrate how the profile shown in FIG. 4A is considered to represent one preferred embodiment of the present invention, a discussion of the inventive background is provided below.

In the obtainment of the preferred profile embodiment represented in FIG. 4A and the corresponding directive means for correcting presbyopia in accordance with the present invention, a series of corrective surgeries were performed. The corrective surgeries can be grouped as follows:

| Group 1: | Treated with a mask | (28 eyes) |
|---|---|---|
| Group 2: | Spheric circular ablation | (163 eyes) |
| Group 3: | Aspheric circular ablation subdivided as: | |
| Subgroup a: | Aspheric Small Zone (OZ) < 1.3 mm, exterior limit > 7.8 mm | (49 eyes) |
| Subgroup b: | Aspheric Medium Zone (OZ) > 1.3 mm, exterior limit < 7.8 mm | (85 eyes) |
| Subgroup c: | Aspheric Large Zone (OZ) > 1.4 mm, exterior limit < 7.8 mm with modified position for the maximum ablation point. | (28 eyes) |
| | TOTAL | (353 eyes) |

Reference is made to FIGS. 3A and 5A–5E which correspond with the various groupings as follows:

FIG. 3A—Mask Treatment of Group 1 (discussed above);
FIG. 5A—Spheric Profile of Group 2;
FIG. 5B—Aspheric Small Zone of Group 3, Subgroup a;
FIG. 5C—Aspheric Medium Zone of Group 3, Subgroup b;
FIG. 5D—Aspheric Large Zone of Group 3, Subgroup c; and
FIG. 5E—Resultant Determination Profile based on work in FIGS. 5A TO 5D.

FIGS. 5A–5B illustrate partial presbyopic correction ablation profiles in somewhat schematic fashion with the two solid vertical lines providing a common reference frame for showing shifts in, for example, the maximum deflection point, made from profile to profile.

The spheric profile of Group 2 is represented by FIG. 5A. As can be seen by FIG. 5A, a relatively large OZ zone is formed (as compared with the zones shown in FIGS. 5B and 5C) with a relatively steep, downward sloped profile section. The steep downward and outward sloped profile section leads to the maximum ablation depth followed by a similarity steep, sloped profile section that slopes up and out away from the maximum ablation depth. The slopes positioned inner and outer of the maximum ablation depth are generally the same and hence the spherical reference. The slope angle is schematically depicted as $\theta_o=25°$.

The aspheric, small OZ of Group 3, Subgroup a) profile shown in FIG. 5B features a reduced OZ, as compared to FIG. 5A and a less steep sloping downward and upward profile leading to and extending from the maximum ablation depth. As also can be seen by FIG. 5B, the maximum ablation depth is shifted outward with respect to that which is shown in FIG. 5B. The system is aspherical as, unlike FIG. 5A, the downward and upping slopes of the profile sections before and after the MD point are different. The slope angles are schematically depicted as $\theta_1=40°$ and $\theta_2=60°$ in FIG. 5B.

FIG. 5C represents Group 3, Subgroup b, which features an OZ with a diameter intermediate of that of the larger OZ in FIG. 5A and the smaller OZ of FIG. 5B. The inward and outward slopes are relatively close to that of FIG. 5B. The increase in OZ with respect to the arrangement in FIG. 5B, results in an additional outward shifting of the maximum ablation depth. The slope angles are schematically represented by $\theta_3=45°$ and $\theta_4=50°$.

FIG. 5D shows an OZ diameter similar to that of FIG. 5A and a similar relatively steep sloping section extending from the periphery of the OZ. Unlike the FIG. 5A arrangement, however, the outward extension of the profile extending away from the maximum ablation depth is of a less steep slope then the arrangement in FIG. 5A. The slopes are schematically represented by $\theta_5=25°$ and $\theta_6=50°$.

FIG. 5E illustrates a graphical representation of the above equation which presents a profile that represents a further evolution of the profile sequence shown in FIGS. 5A–5D, and thus is most similar to the schematic illustration of FIG. 5D. FIG. 5E represents the same profile as depicted in FIG. 4A. The differences in appearance between FIGS. 4A and 5E are based on the fact that the horizontal scales are not in direct correspondence with each other (e.g., the FIG. 5E scale is more compressed than the FIG. 4A scale, resulting in a somewhat more compressed profile appearance in FIG. 5E as compared with FIG. 4A). The FIG. 5E depiction represents an example of what would appear on a computer monitor following input of the desired parameters and determination of the profile using the profile determination means of the control system, while FIG. 4A is more representative of a pre-input or calculated ablation profile configuration such as profile sketch or digital tablet drawing that is scanned for input to a control system.

In a preferred embodiment of the invention, the control system includes means for determining a desirable ablation profile which presents a plurality of fields on a computer monitor screen. These fields contain descriptions of patient measurable base values to be input (e.g., limbus to limbus length) and locations for inputting the correct value through use of a keyboard or the like. As most measurable values do not deviate extensively the field can present a plurality of measurement choices in addition to the possibility of a keyboard input. A plurality of additional fields are also preferably presented which are directed at one or more of the diameters F, G, H and I, and preferably, MD as well Also preferably provided are the aforementioned preferred ranges in mm (and microns for depth) on an appropriate scale (e.g., 0.25 mm scale) for allowing an operator to click on the desired value which once chosen can be fed to an ablation profile formation means for use by the directive means in providing the correct laser output and position on the corneal stroma.

In FIG. 5E, the vertical axis represents the depth of ablation to be carried out and ranges from 0 to 40 μm or 0 to $4\times10^{-5}$ meters and the horizontal axis represents a scale which correlates with the actual ablation locations of the laser system on the eye. On the input side, any scale which can be converted to the appropriate laser contact regions on the eye including values that are in one-to-one correspondence with the measured eye or a scale involving an appropriate conversion factor in going from the illustrated profile to the sculpture ablation in the exposed corneal stroma can be relied upon. The same can also be true on the display side in going from the determined profile to the displayed profile. Preferably, a flying spot laser system (e.g., the flying spot LASERSIGHT "LSX" with a 200 hz speed laser) is used which has the appropriate input or control parameters based on the desired presbyopia correcting profile. This system, which includes a presbyopia correction directive means in accordance with the present invention, is one that helps in greatly reducing the time for ablation and also the post-operative removing, which is perhaps the major inconvenience for the treatment process at the present time.

As noted above, one facet of the present invention has been the comparison of the results for those different groups and the various activities carried out that led to those results, and using that information in the process of providing a desired presbyopic correction profile and associated presbyopia correction directive means. This comparison process has involved the use of the basic eye exams of VASC, VACC, Sphere and Cylinder. Also, the contrast sensitivity analysis is considered one of high importance in the analysis of the results obtained, due to the area of treatment (the central cornea) being an area that is prone to creating controversy of this type on the symptoms for the patient. It is also considered that the variance amount from these tests is a relevant indicator on the recovery time of the patient.

Other important subjective data for the evaluation of the patients are the ghost images, halos, and aberrations, which are very difficult to quantify. The contrast sensitivity analysis noted above is tested for far and near and with day light and night light, glare and haze in different spatial frequencies. It is also worthy of mention that, in the normal course of events, a presbyopic patient shows a diminished contrast sensitivity in comparison to a person of a less age due to particular changes in cornea, lens, and retina. This needs to be taken into account in considering the results of any contrast sensitivity analysis.

In relying on a mask system such as that shown in FIG. 3A, it has been observed that even after four years of the surgery, this group maintains a good and stable far Visual Acuity (VA). This is due, at least in part, to the fact that the induced refractive change is not very significant (+/−0.50). Although the near vision has shown improvement in mask treated individuals, the resultant improvements are less than the desired correction of the inventor (in average 20/50). The stability factor for determining follow up times is of equal significance in any presbyopia correction procedure. At the time the Group A patients were treated, there was not considered to exist the proper tools to analyze the contrast sensitivity. Contrast sensitivity analyzing tools are available presently and were used with post mask groups of patients. Accordingly, the characteristics of the contrast sensitivity for the mask patients was based on discussions with the patients, some of which described symptoms like glare, halos, distortion and night driving problems that only went away after a relatively long period of time (in some patient; more than two years since treatment and a few have symptoms that still persist). In view of this, refinement of the presbyopic treatment and system was carried out.

An initial stage in the refinement process was a presbyopic treatment and system involving the spherical ablation profile of FIG. 5A. The resultant good VA of this group, for both far and near, provided additional data for use in continuing on further refining the presbyopic multifocal correction process and system of the present invention. However, the main disadvantage found using this ablation profile of FIG. 5A is the continued relatively long recovery time needed for symptoms like halos, glare, distortion and night driving. Also, in the same way as it is found in hyperopic LASIK, the patients were noted as having a myopic shift during the immediate post-operative period, most probably due to stromal edema.

In an attempt to reduce the recovery time for the inherent symptoms of the earlier treatments, the profile and corresponding system for forming the desired profile was changed from the spheric ablation configuration of FIG. 5A to an aspheric ablation. As noted above, this general aspheric grouping can be broken down into three subgroups which are described below.

With respect to the aspheric ablation with small OZ <1.3 mm, exterior limit >7.8 mm group, this group was found to be one that produced more undesirable results, as compared with the other illustrated profiles and associated profile forming systems. The major undesirable result as compared with the other profiles was found in a reduction in VA, with and without correction, and marked symptoms like those described above. Although the FIG. 5B results presented very good near vision in quantity, the quality of this was poor due to the symptoms. Even though in the end the patient was found to be myopic, it was common in the early post-operative period to find hyperopia that, if not corrected, would only increase the VA problem. The general problems with this group are felt to be associated mainly with the small OZ that does not leave much room for any decentered ablation without the penalty of significant and undesirable alterations on the surgical outcome.

In the asphiric ablation with medium OZ profile of FIG. 5C, with OZ >1.3 mm and exterior limit <7.8 mm, there was seen an improvement in the VA with and without correction in spite of the highest myopic shift in relation to the other groups, most probably due to the shifting of the maximum ablation point out further from the center of the optical zone. There was also seen an improvement on the symptoms both in quantity and recovery time. As with the other aspheric groups, it also provided good near vision. In an effort to further improve on the symptoms, testing was done in accordance with the subgroup c profile and corresponding system.

In subgroup c, the aspheric ablation and corresponding control systems for forming that ablation profile features a large OZ >1.4 mm with an exterior limit <7.8 mm (most falling on or close to 1.4 mm and 7.8 mm for the respective distances). While there has been less follow up time for this group than with the other groups, there can be seen in comparison with the other groups, that this subgroup c presents less symptoms with less discomfort for the patient and a faster recovery, while still retaining good near and far VA qualities. By moving the maximum ablation point back in toward the center of the OZ, while keeping a relatively steeper internal downward slope as compared to its less sloping outward ablation profile section, there was found to be a reduction in the myopia induced by the earlier treatment without altering the good near vision. This moderate induced myopia reduced only slightly the uncorrected VA for distance.

Under subgroup c), in the actual analysis of the patients treated, with an acceptable post-operative, a significant number (40%) of patients were found not to require far or near optical correction for the treated eye. With respect to all groups and subgroups, there has also been seen a large number of treated bilateral patients that do all of their normal activities without the use of glasses for near or far after surgery. In this group of bilateral patients, treated with a different profile for each eye, there can be seen the progress in the incurred changes represented by the profiles 5A–5E and 4A.

The complications that have been encountered during the various treatments are believed to be due to several different actors such as:

(1) Decentered ablations, which could obviously be the cause for distortions, reduction of the VASC with or without correction;

(2) Oversteepening of the central cornea with frequent occurrences of keratitis, distortion, glare, photophobia and reduction of the VA with and without correction; and (3) Induced astigmatism. Although not a very frequent occurrence due to the surgery, it is more likely related to a decentration of the ablation.

These complications have been shown to be manageable mainly by re-lifting the flap, and with the aid of a laser guided by a topographer on the first post-operative treatment, a reablation to bring the cornea more toward or to the desired shape. In doing this, there has been achieved the reshaping, but in most instances, more than one surgical retouch is necessary when complications are involved. The effectiveness of the enhancements has been demonstrated by the clinicals and the topographies. Various topography systems are available for use such as the EyeSys™ video Topography System, an illustration of which is provided in the aforementioned "Surgery For Presbyopia and Hyperopia" reference. It also has been demonstrated that the re-lifting of the flap has no adverse contraindications, but instead provide a noticeable improvement of the symptoms and on the VA of the patient.

Relatively speaking, the potential disadvantages of the present invention's treatments and systems represented by FIGS. 3A and 5A–5E, for example, are few, especially when considered in view of the possibility of doing away with a requirement for bifocals in many of those treated. The few disadvantages found include:

(1) Slow post-operative recovery sometimes up to a year especially with the early treatments on the symptoms related with light distortion, halos, night glare and in some instances these symptoms will not go away unless a surgical re-intervention is performed. This disadvantage has been lessened significantly in the desired profiles of, for example, FIGS. 4A and 5E;

(2) Monocularity; as in monovision it is a disadvantage that can be easily fixed once the surgery is performed on both eyes; and (3) High percentage of enhancements; this could become a disadvantage, but with the progress made in the changing and the modifying of the surgical profiles, the technique of the present invention is showing a trend to follow up a more normal and stable behavior as with the other refractive surgeries currently in practice.

As to the preferred profile of FIG. 4A used in making the multifocal LASIK ablation for the presbyopia correction, the associated contour control means preferably works in conjunction with a laser system that involves an automatic ablation using a flying spot scanning laser at 200 hz. This type of system will bring some advantages such as:

(1) Better profile; with this kind of ablation there is provided a much better "Physiologic" ablation with much fewer symptoms for the patient and a faster post-operative recover is considered available; and (2) Ablation time; there can be reduced the ablation time from an average of 2 minutes (for a mask operation) to 20 seconds for an automatic ablation system, such as the flying spot laser system with the contour control system of the present invention. This reduction in time is of significance from the standpoint that a direct correlation has been observed between the ablation time and the recovery time. This time efficiency is even more pronounced when there is combined the presbyopic correction treatment of the present invention with myopia, astigmatism or hyperopia treatments.

Under the present invention, once the patient has achieved full patient recovery, one great advantage that has been found with the present invention is the multifocality for the patient that enables them with adequate vision for near and far. Also, while some degree of induced myopia has been seen with the different profiles, there has been found that the VA, with respect to far correction, is better than the average VA for the same degree of myopia on a person that has not undergone the surgery. Also, it can be said that for some patients, in spite of their age, and by ending up slightly hyperopic, they still show a more than acceptable near vision which is a clear indication of an effective multifocality. For the patients with a small residual myopia, they require only little addition for near vision and have all in all better near VA as compared to similar situations found for pseudophakic patients. Thus to summarize, in the follow up of the patients on the different groups, in spite of having from the very beginning a good or bad near VA, they eventually show a clear stability. In the refraction it can be seen that the residual myopic predominant defect is greater during the first weeks and is perhaps due to stromal edema, but this problem has shown improvement from profile to profile for the most part. Another significant advantage of the present invention's presbyopic correction method and system is the possibility to provide good presbyopic correction from the start, regardless of the variations of the presbyopic power that changes with the growing age of the patient.

FIG. 6 provides a schematic illustration of another laser system embodying the present invention. The FIG. 6 illustration represents a modification of the aforementioned VISX Star laser system. This system features an excimer laser 200 as described above which directs a laser beam into contact with Mirror M1 for redirecting the beam into beam integration module 202 for beam refinement before reaching mirror M3. Mirror M3 redirects the beam into beams shaping module 204 with modules 202 and 204 providing two rotating hex prisms between mirrors M1 and the final mirror M3 in an effort to temporarily integrate the beam components for the purpose of smoothing the shape of the beam. In a preexisting VISX Star laser system a hyperopia module is placed between module 204 and mirror M3 to provide to mirror M3 a hyperopia correcting beam function upon reaching the eye 208. In the present invention, the hyperopia module is replaced with presbyopia module 206 that provides, in conjunction with the other beam control features of the illustrated laser system, a presbyopic corrective directive means for forming a desired presbyopia correcting contour with preestablished profile in the exposed corneal stroma of the eye in accordance with the above set forth present invention parameters. The combination of the presbyopic corrective directive means and the preexisting control system of the laser system thus represents the presbyopic correction control means of the present invention.

Also systems such as that described in U.S. Pat. No. 5,395,356 include a monitoring system wherein the degree of ablation is sensed and the control system is altered in an effort to not deviate from the desired ablation contour. The present invention's presbyopia correction control means for forming predetermined removed tissue contours in corneal stromas with its stored profile parameters governed by equation G(X) above, can thus also include means for comparing the sensed parameters against the predetermined parameters involving equation G(X) or some other reference parameter arrangement in accordance with the features of the present invention to provide additional ablation formation control on a real time basis.

While the invention has been described in terms of various preferred embodiments and methods for performing the procedure, those skilled in the art will recognize that various changes and modifications may be made without departing from the spirit and scope of the invention, as defined in the appended claims.

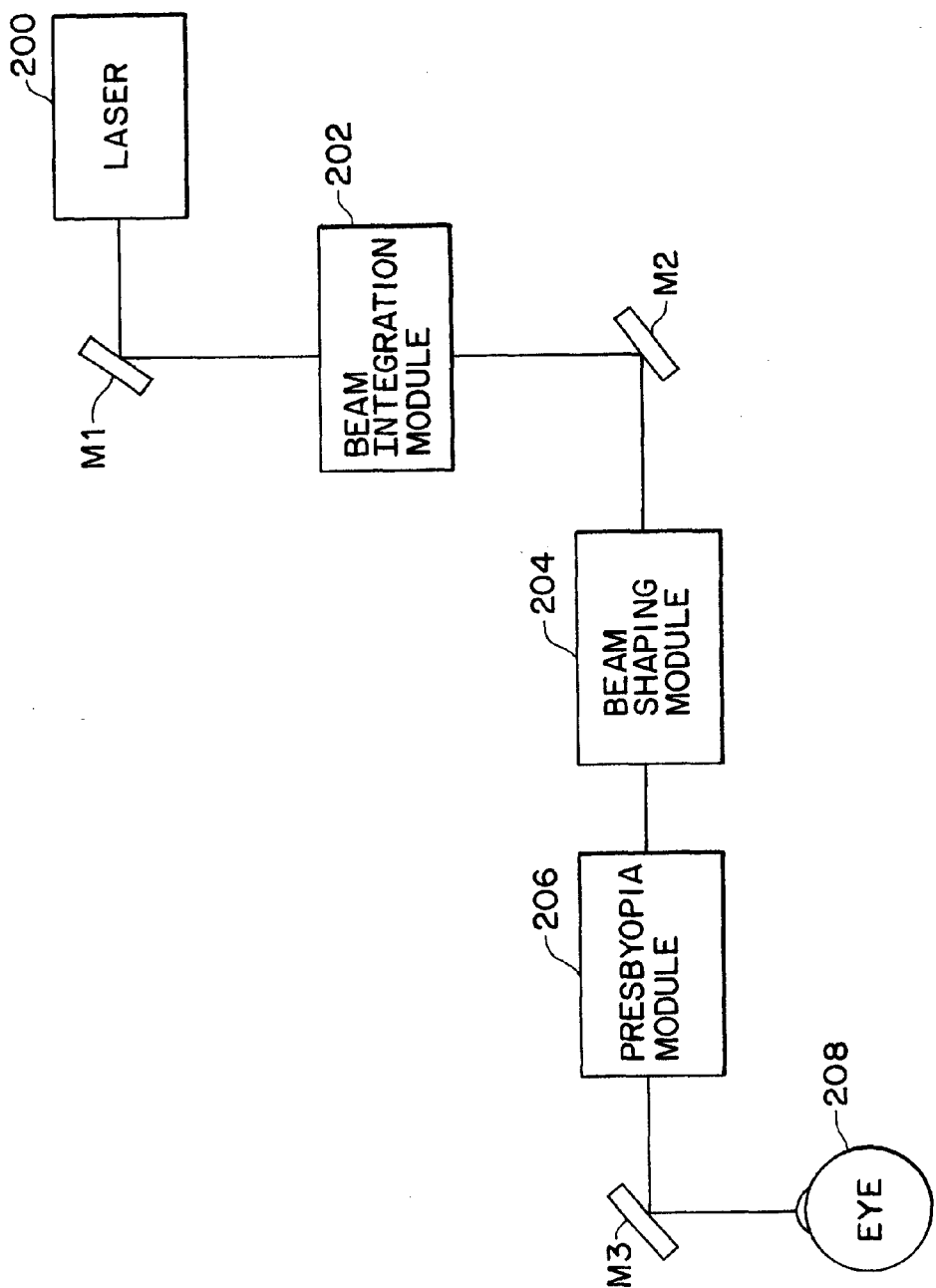

What is claimed is:

1. A presbyopia correction system, comprising:
a corneal stroma tissue removing system which includes means for removing tissue and control means for providing presbyopic correction to an exposed corneal stroma of an eye, and wherein said means for removing tissue includes a laser system and said control means includes directive means for directing a formation by said laser system of an ablation region in said corneal stroma having a central unablated diameter of 1.4 to 1.8 mm.

2. The presbyopia correction system of claim 1 wherein said directive means further includes means for directing a formation by said laser system of the ablation region with a maximum ablation depth circumference having a diameter of 2.4–3.2 mm.

3. The presbyopia correction system of claim 2 wherein said directing means further includes means for forming a maximum ablation depth of 34 to 42 microns.

4. The presbyopia correction system of claim 3 wherein said means for directing ablation includes means for limiting the outer circumference of the ablated treatment area to 7.0 to 7.8 mm.

5. The prebyopic correction system of claim 1 wherein said control means includes directive means for formation of an annular ablation region in the corneal stroma which utilizes a profile represented by the following:

$$G(X)=F(X)+F(X)*(k_3/10+factor/k_3)*arctan\ (factor-1).$$

6. The presbyopia correction system of claim 1 wherein said directive means includes a presbyopia correction module positioned between the laser source and the corneal stroma being treated.

7. The presbyopia correction system of claim 6 wherein said correction module includes an erodible mask.

8. The presbyopia correction system of claim 6 wherein said correction module includes means for altering a laser beam configuration or path.

9. The presbyopia correction system of claim 8 wherein said means for altering includes a moving mask assembly.

10. The presbyopia correction system of claim 8 wherein said means for altering includes a mirror assembly having a mirror directing a laser beam in uninterrupted fashion to the corneal stroma.

11. The presbyopia correction system of claim 1 wherein said directive means includes a software or hardware component of a laser position control system.

12. The presbyopia correction system of claim 11 wherein the software or hardware component has a profile formation means which forms a profile representation for use by a laser beam positioning system.

13. The presbyopia correction system of claim 12 wherein the profile formation means includes reception means for receiving input data, with the input data including individual patient eye measurement data.

14. The presbyopia correction system of claim 12 wherein the profile formation means includes reception means for receiving input data, with the input data includes profile value parameters.

15. The presbyopia correction system of claim 14 wherein the reception means is designed to receive input data that includes selections from a plurality of ranges of values corresponding to values used by the profile formation means.

16. The presbyopia correction system of claim 14 wherein the reception means is designed to receive an input value from one or more of the following ranges:
a). 1.4–1.8 mm for the diameter value of a central most region of the corneal stroma to remain unablated;
b). 2.4–3.2 mm for an outer diameter of a maximum ablation depth ring;
c). 7.0–7.8 mm for an outer diameter of a total ablation treatment region of the corneal stroma; and
d). 34 to 42 microns for a maximum ablation depth at the maximum ablation depth ring.

17. The presbyopia correction system of claim 16 wherein said reception means is designed to receive a value directed at least three of a–d above.

18. The presbyopic correction system of claim 1 wherein said directive means directs ablation region formation based on an ablation level profile with the following parameters a–d:
a). 1.4–1.8 mm for the diameter value of a central most region of the corneal stroma to remain unablated;
b). 2.4–3.2 mm for an outer diameter of a maximum ablation depth ring;
c). 7.0–7.8 mm for an outer diameter of a total ablation treatment region of the corneal stroma; and
d). 34 to 42 microns for a maximum ablation depth at the maximum ablation depth ring.

19. The presbyopic correction system of claim 18 wherein at least one of parameters a–c above is based on a central reference point that is one unit superior and one unit nasal to a center point of a pupil, with each unit represented by one third of the radius of a circle defined by the pupil.

20. The presbyopia correction system as recited in claim 1 wherein said directive means directs corneal stroma ablation based on an aspherical ablation profile section that extends outward of the central unablated region and has an interior sloped section leading to a maximum ablation point; and a less steep exterior sloped section extending externally to the maximum ablation point.

21. The presbyopia correction system as recited in claim 20 wherein each of said interior and exterior sloped sections have curved slope profiles.

22. A presbyopic corrective software or hardware package that comprises data store means and directive means for directing a formation of a predetermined ablation corneal stroma profile in accordance with parameters a–b which are as follows:
a). 1.4–1.8 mm for the diameter value of a central most region of the corneal stroma to remain unablated; and
b). 2.4–3.2 mm for an outer diameter of a maximum ablation depth ring.

23. The presbyopic software or hardware package of claim 22 wherein said directive means determines an ablation profile represented at least in part on the following formula:

$$G(X)=F(X)+F(X)*(k_3/10+factor/k_3)*arctan\ (factor-1).$$

24. The presbyopic corrective module as recited in claim 22 wherein said means for directing is based on an ablation profile having one of the additional parameters c) and d) which are as follows:

c). 7.0–7.8 mm for an outer diameter of a total ablation treatment region of the corneal stroma, d). 32 to 42 microns for a maximum ablation depth at the maximum ablation depth ring.

25. The presbyopic correction method as recited in claim 24 wherein said means for directing a formation includes parameters represented by each of a) to d).

26. The presbyopic corrective software or hardware package as recited in claim 22 wherein said package is software stored on a processor readable medium.

27. A method for providing a presbyopia corrective system comprising installing the presbyopic corrective software or hardware package of claim 22 in a laser system.

28. A method for correcting presbyopia; comprising:

resecting a portion of a cornea of an eye to expose corneal stroma tissue;

ablating the corneal stroma tissue with the system of claim 1; and repositioning the resected portion of the cornea of the eye.

29. A method for facilitating presbyopia correction comprising forming an ablation region in a corneal stroma based on an ablation profile having an aspherical ablation profile segment extending in a maximum ablation zone with a parameter of said ablation profile including at least one member selected from parameters a–d which are as follows:

a). 1.4–1.8 mm for the diameter value of a central most region of the corneal stroma to remain unablated;

b). 2–4–3.2 mm for an outer diameter of a maximum ablation depth ring;

c). 7–0–7.8 mm for an outer diameter of a total ablation treatment region of the corneal stroma;

d). 34 to 42 microns for a maximum ablation depth at the maximum ablation depth ring.

30. The method of claim 29 wherein said method includes forming an annular ablation region with a laser system with a cross-section profile of that ablation region having 2 or more of the parameters a) to d) above.

31. The method of claim 29 wherein forming the ablation region includes using all of parameters a)–d).

32. The method of claim 29 wherein forming the ablation region includes relying on the following ablation region profile representation:

$G(X)=F(X)+F(X)*(k_3/10+factor/k_3)*arctan\ (factor-1).$

33. A presbyopia correction system, comprising:

a corneal stroma tissue removing system which includes means for removing tissue and control means for providing presbyopic correction to an exposed corneal stroma of any eyes and wherein said control means includes directive means for formation of an annular ablation region in the corneal stroma which utilizes a profile represented by the following:

$G(X)=F(X)+F(X)*(k_3/10+factor/k_3)*arctan\ (factor-1).$

34. A method for facilitating presbyopia correction comprising forming an ablation region in a corneal stroma having a profile cross-section with a parameter that is a member selected from the group consisting of:

a) 1.4–1.8 mm for the diameter value of a central most region of the corneal stroma to remain unablated;

b) 2.4–3.2 mm for an outer diameter of a maximum ablation depth ring;

c) 7.0–7.8 mm for an outer diameter of a total ablation treatment region of the corneal stroma;

d) 34 to 42 microns for a maximum ablation depth at the maximum ablation depth ring; and e) a combination thereof; and wherein forming the ablation region includes relying on the following ablation region profile representation:

$G(X)=F(X)+F(X)*(k_3/10+factor/k_3)*arctan\ (factor-1).$

35. A presbyopic corrective component for use with an eye laser system that comprises data storage means and directing means for directing a formation of an ablation profile in accordance with parameters a–d which are as follows:

a) 1.4–1.8 mm for the diameter value of a central most region of the corneal stroma to remain unablated;

b) 2.4–3.2 mm for an outer diameter of a maximum ablation depth ring;

c) 7.0–7.8 mm for an outer diameter of a total ablation treatment region of the corneal stroma; and d) 34 to 42 microns for a maximum ablation depth at the maximum ablation depth at the maximum ablation depth ring; and wherein said directing means directing means directs an ablation profile based at least in part on the following formula:

$G(X)=F(X)+F(X)*(k_3/10+factor/k_3)*arctan\ (factor-1).$

36. A presbyopic corrective module that comprises means for receiving a laser beam and means for modifying the received laser beam for directing a formation of a corneal stroma ablation of a predetermined profile in accordance with parameters a–d which are as follows:

a) 1.4–1.8 mm for the diameter value of a central most region of the corneal stroma to remain unablated;

b) 2.4–3.2 for an outer diameter of a maximum ablation depth ring;

c) 7.0–7.8 mm for an outer diameter of a total ablation treatment region of the corneal stroma; and d) 34 to 42 microns for a maximum ablation depth at the maximum ablation depth ring; and wherein said predetermined profile is represented at least in part by the following formula:

$G(X)=F(X)+F(X)*(k_3/10+factor/k_3)*arctan\ (factor-1).$

37. A presbyopia collection system, comprising:

a corneal stroma tissue removing system which includes means for removing tissue and control means for providing presbyopic correction to an exposed corneal stroma a of an eye, and wherein said control means includes directive means for forming a predetermined ablation region in said corneal stroma based on an ablation profile having at least two of the following parameters a–d:

a) 1.4–1.8 mm for the diameter value of a central most region of the corneal stroma to remain unablated;

b) 2.4–3.2 mm for an outer diameter of a maximum ablation depth ring;

c) 7.0–7.8 mm for an outer diameter of a total ablation treatment region of the corneal stroma; and (d) 34 to 42 microns for a maximum ablation depth at the maximum ablation depth ring.

38. The presbyopia correction system as recited in claim 37 wherein said directive means includes a software or hardware component.

39. The presbyopia correction system as recited in claim 37 wherein the directive means includes an additional parameter of having an aspherical maximum ablation zone profile having an inner and outer sloped ablation profile segments which converge to a point of maximum ablation.

40. The presbyopia corrective means as recited in claim 39 wherein said inner sloped ablation profile segment has a steeper slope than said outer sloped ablation profile segment.

41. The presbyopia correction system as recited in claim 40 wherein said inner ablation profile segment includes a concave segment and said outer ablation profile segment includes a convex shape and is longer in length then said inner ablation profile segment.

42. A presbyopia correction system, comprising:
a corneal stroma tissue removing system which includes means for removing corneal stroma tissue and control means for providing presbyopic correction to an exposed corneal stroma of an eye and wherein said means for removing tissue includes a laser system and said control means includes directive means for directing a formation by said laser system of an ablation region, and wherein said ablation region is based on an ablation profile which includes an ablation avoidance central zone having a central reference point which is off-centered with respect to an optimal axis of a pupil of an eye, with the central reference point being within a nasal-superior quadrant of the pupil of the eye; and
an information converter for converting received information concerning the eye to establish the central reference point within the nasal superior quadrant of the eye for use by the said means for directing a formation by said laser system of an ablation region.

43. The presbyopic correction system of claim 42 wherein said central reference point is one unit superior and one unit nasal to a center point of the pupil with each unit represented by one third of the radius of a circle defined by the pupil.

44. The presbyopia correction system of claim 43 wherein said means for directing a formation includes means for forming an ablation ring with aspherical side walls based on an ablation profile with an inner sloped region originating and extending outward from said central zone, with the central zone having a diameter of 1.4 mm to 1.8 mm and a central point corresponding with said central reference point.

45. The presbyopia correction system of claim 44 wherein said sloped regions extend toward one another to define a maximum ablation depth profile region having a diameter of 2.4–3.2 mm and a central point corresponding with said central reference point, and a 34 to 42 micron maximum ablation depth.

46. The presbyopic correction system of claim 42 wherein said information converter receives pupil characteristic data, converts the pupil characteristic data into center point information, and exports information for use by said means for directing a formation by said laser system of an ablation region.

47. The presbyopic correction system of claim 42 further comprising pupil measuring means for measuring pupil characteristic data, and said pupil measuring means being in input communication with said information converter such that said information converter automatically receives input pupil characteristic data from said pupil measuring means and determines center point information based on an analysis of the input data and exports center point information to a reference location system of said laser system.

48. A presbyopic correction system, comprising:
a corneal stroma tissue removing system which includes a laser system;
control means for controlling energy application by said laser system with respect to a preexposed corneal stroma, with said control means including directive means for defining a corneal stroma ablation pattern in the stroma based on an ablation profile which includes an ablation avoidance central zone having a diameter 1.3 or greater and a maximum ablation depth zone extending from a periphery of the central zone and including a first sloped profile section extending downward to a maximum ablation point of the profile, and said profile having a second sloped profile section extending upward from the maximum ablation point, and wherein said first slope is steeper than said second slope and shorter in length.

49. The presbyopic correction system of claim 48 wherein said second sloped section has a convex profile in going from the point of maximum deflection to an upper peripheral end.

50. The presbyopic correction system of claim 48 wherein said central zone is centered so as to be offset from a central optical axis of a pupil of the eye within a nasal-superior quadrant of the pupil.

51. The presbyopic correction system of claim 50 wherein the central reference point is one unit nasal and one unit superior to a center point of a pupil, with each unit represented by one third of the radius of a circle defined by the pupil.

52. The presbyopia correction system of claim 48 wherein said directive means further directs a formation by said laser system of a maximum ablation depth of 38–42 microns.

53. A presbyopia correction method, comprising:
determining a center reference point within a nasal-superior quadrant of the pupil of the eye; and
removing exposed corneal stroma of an eye with a laser system by directing a formation by said laser system of an ablation region based on an ablation profile which includes an ablation avoidance central zone having the central reference point which is off-centered with respect to an optical axis of a pupil of an eye and within the nasal-superior quadrant of the pupil of the eye.

54. The presbyopic correction system of claim 53 wherein direct a formation of an ablation region includes establishing the central reference point at one unit superior and one unit nasal to a center point of the pupil with each unit represented by one third of the radius of a circle defined by the pupil.

55. The presbyopia correction system of claim 53 wherein directing a formation includes forming an ablation ring with aspherical side walls based on an ablation profile with an inner sloped region originating and extending outward from said central zone.

56. A presbyopia correction system, comprising:
a corneal stroma tissue removing system which includes means for removing corneal stroma tissue and control mews for providing presbyopic correction to an exposed corneal stroma of an eye and wherein said means for removing tissue includes a laser system and said control means includes directive means for directing a formation by said laser system of in ablation region, and wherein said ablation region is based on an ablation profile which includes an ablation avoidance central zone having a central reference point which is off-centered with respect to an optical axis of a pupil of an eye, with the central reference point being within a nasal-superior quadrant of the pupil of the eye, and wherein directing a formation includes forming an ablation ring about the central zone with the central zone having a diameter of 1.4 mm to 1.8 mm and a central point corresponding with said central reference point.

* * * * *

UNITED STATES PATENT AND TRADEMARK OFFICE
CERTIFICATE OF CORRECTION

PATENT NO. : 6,302,877 B1
DATED : October 16, 2001
INVENTOR(S) : Ruiz

It is certified that error appears in the above-identified patent and that said Letters Patent is hereby corrected as shown below:

Title page,
The title page should be deleted and substituted with the attached title page.

Drawings
Figs. 4, 4a, 5a-5e, 6 and 7 with the attached Figs. 4, 4a, 5a-5e, 6 and 7.

Signed and Sealed this

Fourteenth Day of May, 2002

Attest:

Attesting Officer

JAMES E. ROGAN
Director of the United States Patent and Trademark Office

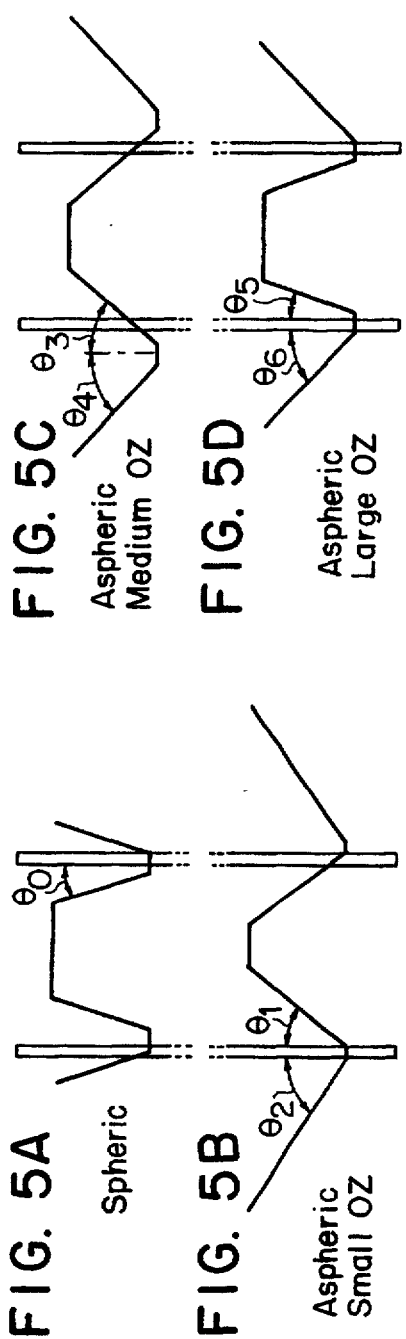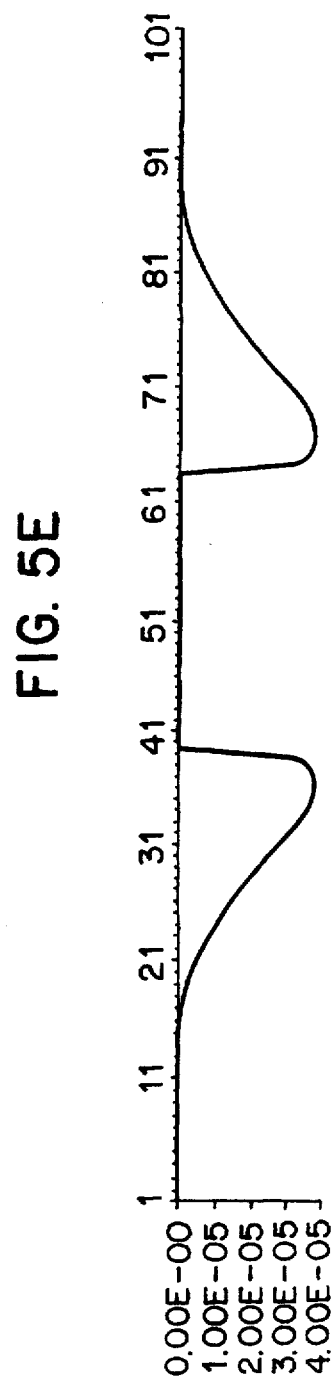
FIG. 5A Spheric
FIG. 5B Aspheric Small OZ
FIG. 5C Aspheric Medium OZ
FIG. 5D Aspheric Large OZ
FIG. 5E

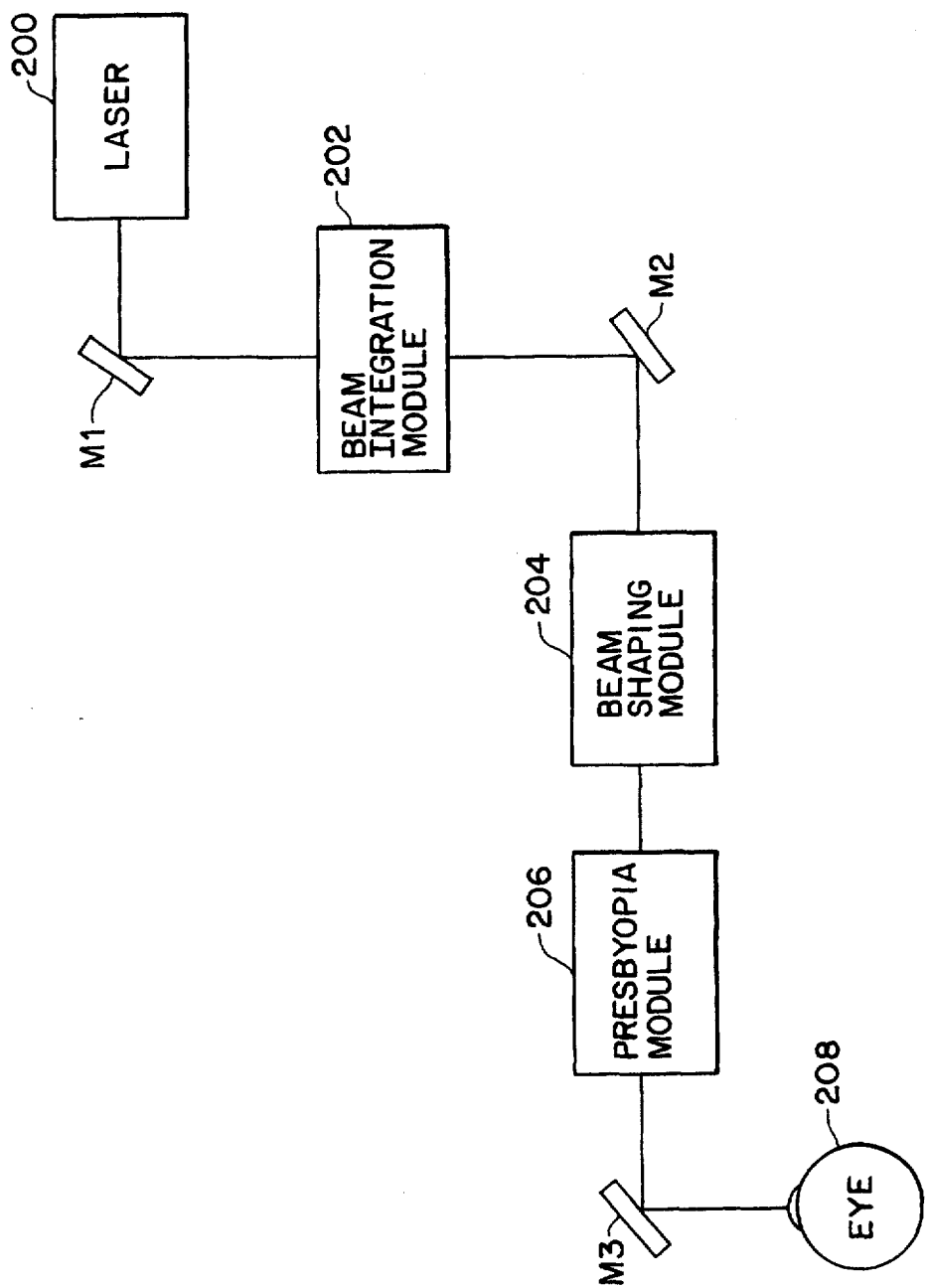

UNITED STATES PATENT AND TRADEMARK OFFICE
CERTIFICATE OF CORRECTION

PATENT NO.    : 6,302,877 B1
DATED         : October 16, 2001
INVENTOR(S)   : Ruiz It is certified that error appears in the above-identified patent and that said Letters Patent is hereby corrected as shown below:

Title page,
The title page should be deleted and substituted with the attached title page.

Drawings
Figs. 4, 4a, 5a-5e, 6 and 7 with the attached Figs. 4, 4a, 5a-5e, 6 and 7.

This certificate supercedes certificate of correction issued May 14, 2002.

Signed and Sealed this

Twentieth Day of August, 2002

Attest:

Attesting Officer

JAMES E. ROGAN
Director of the United States Patent and Trademark Office

(12) United States Patent
Ruiz

(10) Patent No.: US 6,302,877 B1
(45) Date of Patent: *Oct. 16, 2001

(54) APPARATUS AND METHOD FOR PERFORMING PRESBYOPIA CORRECTIVE SURGERY

(76) Inventor: Luis Antonio Ruiz, Centro Oftalmólogico Colombiano, Carrera 20 No. 85-11, Pisos 5o. -6o., Santafé de Bogotá, D.C. (CO)

( * ) Notice: Subject to any disclaimer, the term of this patent is extended or adjusted under 35 U.S.C. 154(b) by 0 days.

This patent is subject to a terminal disclaimer.

(21) Appl. No.: 09/186,884

(22) Filed: Nov. 6, 1998

Related U.S. Application Data

(63) Continuation-in-part of application No. 08/660,376, filed on Jun. 7, 1996, now Pat. No. 5,928,129, which is a continuation-in-part of application No. 08/268,182, filed on Jun. 29, 1994, now Pat. No. 5,533,997.

(51) Int. Cl.$^7$ .................................................. H61N 5/06
(52) U.S. Cl. ................................................................ 606/5
(58) Field of Search ........................... 606/3, 5, 7, 10

(56) References Cited

U.S. PATENT DOCUMENTS 4,173,980 11/1979 Curtain .

(List continued on next page.)

FOREIGN PATENT DOCUMENTS

A-346116 12/1989 (EP) .

(List continued on next page.)

OTHER PUBLICATIONS

*Lasers in Surgery and Medicine*, vol. 10, No. 5, Jan. 1, 1990, pp. 463–468, XP 000385912, Pallikaris: "Laser In–Situ Keratomileusis".

(List continued on next page.)

*Primary Examiner*—Robert L. Nasser, Jr.

(57) ABSTRACT

A system and process for correcting presbyopia with the system including a tissue removal system that preferably includes a laser system with means for forming a predetermined presbyopia correction contour corresponding to a predetermined ablation profile through controlled ablation of an exposed corneal stroma area of the eye such that a central zone of about 1–3 mm or, more preferably, 1.4 to 1.8 mm is left intact with a main, maximum presbyopia ablation zone bordering the untouched or hardly touched (e.g., a radiused transition edge) central zone. The annular maximum ablation zone in the stroma is defined by a smoothly curving, steep profile section which extends out from a central, non-ablation section of the profile. Further outward from the maximum ablation zone in the stroma is an annular treatment zone that is determined by a further section of the presbyopia correcting profile generally represented by a smoothing transition section that extends into another zone which is an unablated zone. The method and device for controlling the formation of the desired corneal stroma configuration preferably involves a presbyopic corrective module based on a predetermined profile determining equation that utilizes certain inputs which preferably include values determined by eye measurements and, preferably, also values pulled from a plurality of zone diameter ranges and a range for maximum depth. The manner in which this profile controlling information is implemented in the ablation or tissue removal process is preferably provided by modification of a present control system of one or more preexisting laser systems such as those used in hyperopia and myopia correction procedures. This modification can include, for example, an added software or hardware module, the formation of a mask with or without a mask movement assembly, or the formation of a suitable mold or shaping device for forming, for example, an erodible mask that can input the desired contour to the exposed corneal stroma. The system and apparatus of the present invention also preferably involve a microkeratome or the like for forming resections in the eye to expose the corneal stroma. A positioning marker, cleaning system and drying system are also preferably used in the present invention to facilitate, for example, corneal flap formation, laser positioning, flap repositioning on a clean surface following ablation and providing a dry corneal stroma surface to the ablating laser. With the system and method of the present invention there is provided a way to efficiently and safely correct problems associated with presbyopia while retaining good near and far vision capabilities and with reduced undesirable postoperative symptoms.

56 Claims, 7 Drawing Sheets

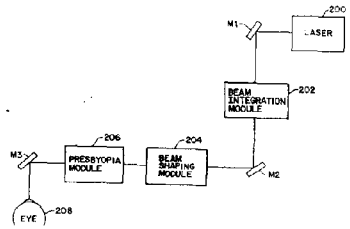

FIG. 6

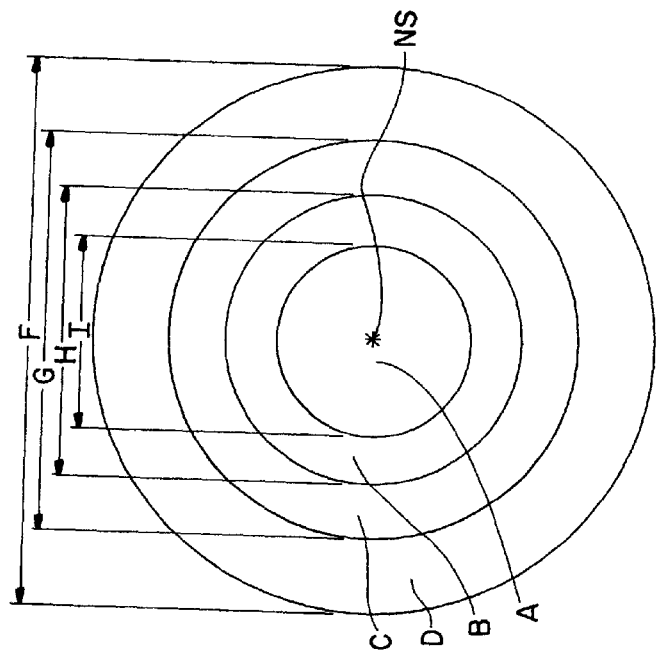
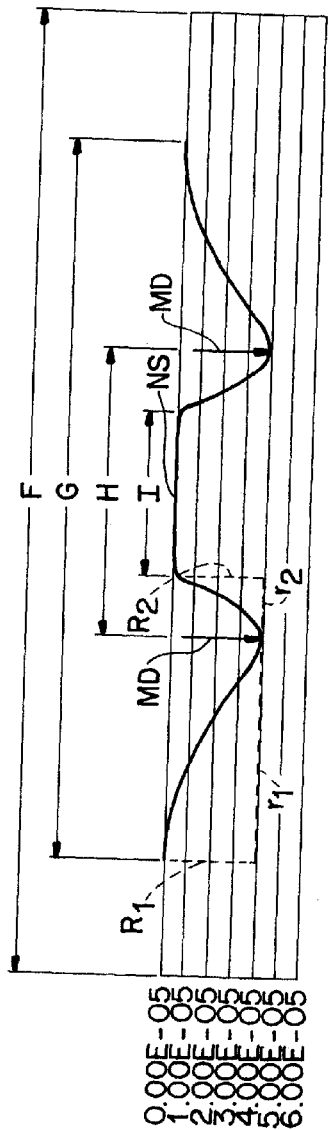
FIG. 4
FIG. 4A

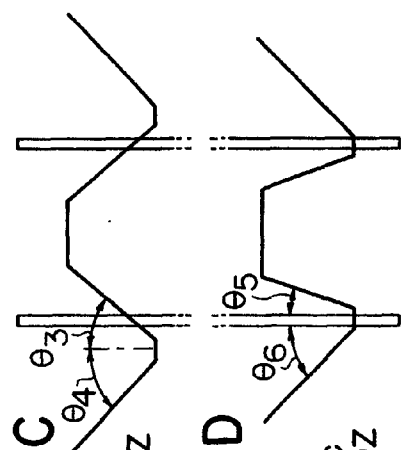
FIG. 5A Spheric
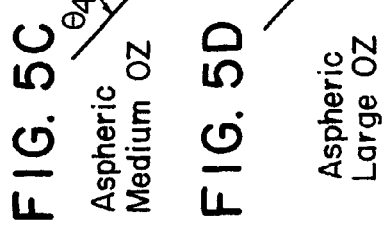
FIG. 5B Aspheric Small OZ
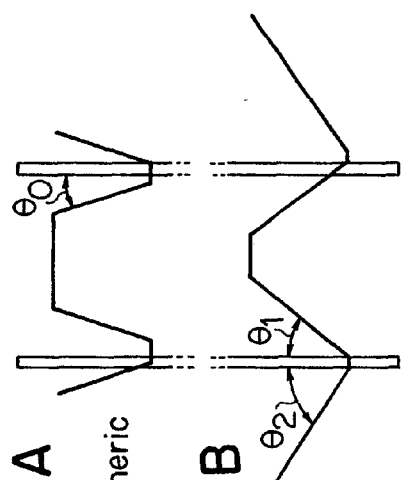
FIG. 5C Aspheric Medium OZ
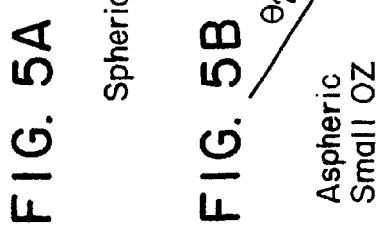
FIG. 5D Aspheric Large OZ
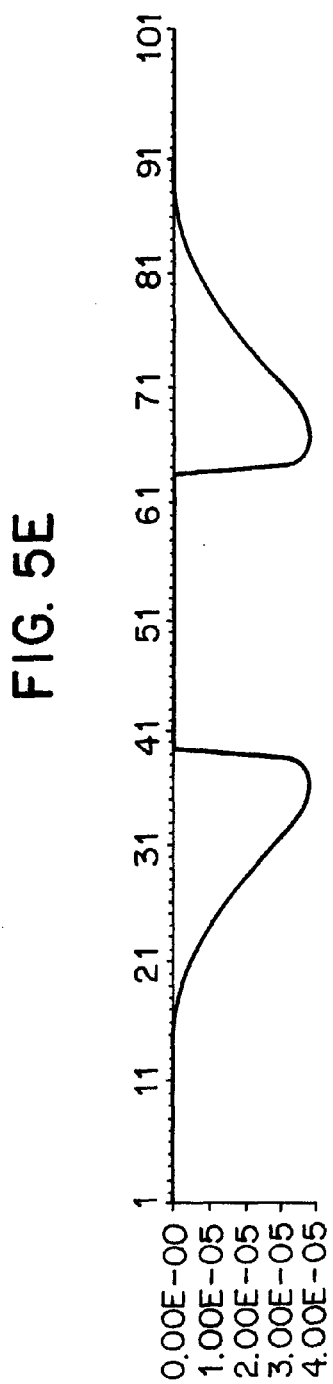
FIG. 5E